US007741531B2

(12) United States Patent
Baltz et al.

(10) Patent No.: US 7,741,531 B2
(45) Date of Patent: Jun. 22, 2010

(54) METHOD FOR MODIFYING GENE EXPRESSION OF A PHYTOPATHOGENIC FUNGUS

(75) Inventors: Rachel Baltz, Lyons (FR); Raphael Dumain, Lyons (FR); Stéphane Peyrard, Caluire et Cuire (FR); Jean-Marc Ferullo, Berlin (DE); Roland Beffa, Saint Genis Laval (FR)

(73) Assignee: Bayer S.A.S. (FR)

( * ) Notice: Subject to any disclaimer, the term of this patent is extended or adjusted under 35 U.S.C. 154(b) by 604 days.

(21) Appl. No.: 11/471,956

(22) Filed: Jun. 21, 2006

(65) Prior Publication Data

US 2007/0061918 A1    Mar. 15, 2007

Related U.S. Application Data

(63) Continuation-in-part of application No. PCT/FR2004/003312, filed on Dec. 20, 2004.

(30) Foreign Application Priority Data

Dec. 23, 2003 (FR) .................... 03 15228
Jul. 2, 2004 (FR) .................... 04 07373

(51) Int. Cl.
  C12N 15/82 (2006.01)
  C12N 15/87 (2006.01)
  A01H 1/00 (2006.01)
(52) U.S. Cl. ............ 800/279; 800/286; 800/285
(58) Field of Classification Search ............ None
See application file for complete search history.

(56) References Cited

U.S. PATENT DOCUMENTS 6,506,559 B1 * 1/2003 Fire et al. .................... 435/6

FOREIGN PATENT DOCUMENTS

WO   WO 99/32619   7/1999
WO   WO 00/26346   5/2000
WO   WO 01/96584 A3   12/2001

OTHER PUBLICATIONS

Kadotani et al. Sep. 2003, MPMI 16:769-776.*
Kusaba et al. Jun. 2003, The Plant Cell 15:1455-1467.*
Waterhouse et al., Nov. 1998, "Virus Resistance and Gene Silencing in Plants can be Induced by Simultaneous Expression of Sense and Antisense RNA." Proceedings of the National Academy of Sciences of USA. (95): 13959-13964.
Tang, Guiliang, Brenda J. Reinhart, David P. Bartel and Philip D. Zamore, 2003, "A Biochemical Framework for RNA Silencing in Plants." Genes & Development. (17, No. 1): 49-63.
Kadotani, Naoki, Hitoshi Nakayashiki, Yukio Tosa and Shigeyuki Mayama, Mar. 24, 2003, "RNA Silencing in the Phytopathic Fungus Magnaporthe oryzae." Molecular Plant-Microbe Interactcions: MPMI. (16): 769-776.

* cited by examiner

Primary Examiner—Anne Kubelik
Assistant Examiner—Li Zheng
(74) Attorney, Agent, or Firm—Connolly Bove Lodge & Hutz LLP

(57) ABSTRACT

The present invention relates to a system for controlling the development of fungi during a phytopathogenic attack which enables the plant to express a construct for inhibiting the expression of a gene essential to the development or to the pathogenicity of the fungus. The technology used is based on the mechanism of RNA interference. The present invention provides methods for producing plants resistant to a phytopathogenic fungus, plant cells and plants resistant to a phytopathogenic fungus, and methods of identifying a gene essential to the development or to the pathogenicity of a phytopathogenic fungus.

36 Claims, 7 Drawing Sheets

(A) Symptom type 1

(B) Symptom type 2

(C) Symptom type 3

(D) Symptom type 4

(E) Symptom type 5

(F) Symptom type 5 (a)

```
                         SEQUENCE LISTING

<160> NUMBER OF SEQ ID NOS: 17

<210> SEQ ID NO 1
<211> LENGTH: 717
<212> TYPE: DNA
<213> ORGANISM: Cercospora nicotianae

<400> SEQUENCE: 1
atcgataacg aggccctcta cgatatctgc atgcgcaccc tgaagctgtc caacccctcc    60
tacggtgacc tcaactacct tgtttctgct gttatgtccg gtgtcaccac ctgtctccgt   120
ttccccggtc agctgaactc cgacctccga aagctcgccg tcaacatggt gcctttccct   180
cgtctacact tcttcatggt cggctttgct cctctgacca gccgtggtgc tcactctttc   240
cgcgctgtca gcgttcctga gttgacccaa cagatgttcg accccaagaa catgatggct   300
gcttcggact tccgcaacgg tcgctacctg acctgctcgg ccattttccg tggccgtgtc   360
gctatgaagg aggtcgagga ccagatgcgc aacgtccaga gcaagaactc gtcttacttc   420
gttgaatgga ttcccaacaa tatccagaca gcccttttgtg ccatccctcc ccgaggactt   480
acgatgtctt cgaccttcat cggaaactcc acctctatcc aggagctctt caagcgcgtt   540
ggtgagcagt tcactgccat gttccgacgc aaggctttct tgcattggta tactggtgag   600
ggtatggacg agatggagtt cactgaggct gagtccaaca tgaacgatct tgtctccgaa   660
taccagcagt accaggatgc tggtattgat gaggaggaag aggagtacga ggaggag      717

<210> SEQ ID NO 2
<211> LENGTH: 874
<212> TYPE: DNA
<213> ORGANISM: artificial sequence
<220> FEATURE:
<223> OTHER INFORMATION: synthetic gene

<400> SEQUENCE: 2
gtactcgagt cgcgacgtac gttcgaacaa ttggtttaaa cgcccgggca cgtgggatcc    60
aagcttatcg atttcgaacc caatttccca actgtaatca atccaaatgt aagatcaatg   120
ataacacaat gacatgatct atcatgttac cttgtttatt catgttcgac taattcattt   180
aattaatagt caatccattt agaagttaat aaaactacaa gtattattta gaaattaata   240
agaatgttga ttgaaaataa tactatataa aatgatagat cttgcgcttt gttatattag   300
cattagatta tgttttgtta cattagatta ctgtttctat tagtttgata ttatttgtta   360
ctttagcttg ttatttaata ttttgtttat tgataaatta caagcagatt ggaatttcta   420 acaaatatt tattaacttt taaactaaaa tatttagtaa tggtatagat atttaattat   480
ataataaact attaatcata aaaaaatatt attttaattt atttattctt atttttacta   540
```

-continued

```
tagtatttta tcattgatat ttaattcatc aaaccagcta gaattactat tatgattaaa    600
acaaatatta atgctagtat atcatcttac atgttcgatc aaattcatta aaaataatat    660
acttactctc aacttttatc ttcttcgtct tacacatcac ttgtcatatt tttttacatt    720
actatgttgt ttatgtaaac aatatattta taaattattt tttcacaatt ataacaacta    780
tattattata atcatactaa ttaacatcac ttaactattt tatactaaaa ggaaaaaaga    840
aaataattat ttccttacca attggggtac ctac                                874
```

<210> SEQ ID NO 3
<211> LENGTH: 717
<212> TYPE: DNA
<213> ORGANISM: Cercospora nicotianae

<400> SEQUENCE: 3

```
ctcctcctcg tactcctctt cctcctcatc aataccagca tcctggtact gctggtattc     60
ggagacaaga tcgttcatgt tggactcagc ctcagtgaac tccatctcgt ccataccctc    120
accagtatac caatgcaaga aagccttgcg tcggaacatg gcagtgaact gctcaccaac    180
gcgcttgaag agctcctgga tagaggtgga gtttccgatg aaggtcgaag acatcgtaag    240
tcctcgggga gggatggcac aaagggctgt ctggatattg ttgggaatcc attcaacgaa    300
gtaagacgag ttcttgctct ggacgttgcg catctggtcc tcgacctcct tcatagcgac    360
acggccacgg aaaatggccg agcaggtcag gtagcgaccg ttgcggaagt ccgaagcagc    420
catcatgttc ttggggtcga acatctgttg ggtcaactca ggaacgctga cagcgcggaa    480
agagtgagca ccacggctgg tcagaggagc aaagccgacc atgaagaagt gtagacgagg    540
gaaaggcacc atgttgacgg cgagctttcg gaggtcggag ttcagctgac cggggaaacg    600
gagacaggtg gtgacaccgg acataacagc agaaacaagg tagttgaggt caccgtagga    660
ggggttggac agcttcaggg tgcgcatgca gatatcgtag agggcctcgt tatcgat       717
```

<210> SEQ ID NO 4
<211> LENGTH: 2308
<212> TYPE: DNA
<213> ORGANISM: artificial sequence
<220> FEATURE:
<223> OTHER INFORMATION: synthetic gene

<400> SEQUENCE: 4

```
atcgataacg aggccctcta cgatatctgc atgcgcaccc tgaagctgtc caacccctcc     60
tacggtgacc tcaactacct tgtttctgct gttatgtccg gtgtcaccac ctgtctccgt    120
ttccccggtc agctgaactc cgacctccga aagctcgccg tcaacatggt gcctttccct    180
cgtctacact tcttcatggt cggctttgct cctctgacca gccgtggtgc tcactctttc    240
cgcgctgtca gcgttcctga gttgacccaa cagatgttcg accccaagaa catgatggct    300
gcttcggact tccgcaacgg tcgctacctg acctgctcgg ccattttccg tggccgtgtc    360
gctatgaagg aggtcgagga ccagatgcgc aacgtccaga gcaagaactc gtcttacttc    420
gttgaatgga ttcccaacaa tatccagaca gccctttgtg ccatccctcc ccgaggactt    480
acgatgtctt cgaccttcat cggaaactcc acctctatcc aggagctctt caagcgcgtt    540
ggtgagcagt tcactgccat gttccgacgc aaggctttct tgcattggta tactggtgag    600
ggtatggacg agatggagtt cactgaggct gagtccaaca tgaacgatct tgtctccgaa    660
taccagcagt accaggatgc tggtattgat gaggaggaag aggagtacga ggaggaggta    720
```

-continued

```
ctcgagtcgc gacgtacgtt cgaacaattg gtttaaacgc ccgggcacgt gggatccaag    780
cttatcgatt tcgaacccaa tttcccaact gtaatcaatc caaatgtaag atcaatgata    840
acacaatgac atgatctatc atgttacctt gtttattcat gttcgactaa ttcatttaat    900
taatagtcaa tccatttaga agttaataaa actacaagta ttatttagaa attaataaga    960
atgttgattg aaaataatac tatataaaat gatagatctt gcgctttgtt atattagcat   1020
tagattatgt tttgttacat tagattactg tttctattag tttgatatta tttgttactt   1080
tagcttgtta tttaatattt tgtttattga taaattacaa gcagattgga atttctaaca   1140
aaatatttat taacttttaa actaaaatat ttagtaatgg tatagatatt taattatata   1200
ataaactatt aatcataaaa aaatattatt ttaatttatt tattcttatt tttactatag   1260
tattttatca ttgatattta attcatcaaa ccagctagaa ttactattat gattaaaaca   1320
aatattaatg ctagtatatc atcttacatg ttcgatcaaa ttcattaaaa ataatatact   1380
tactctcaac ttttatcttc ttcgtcttac acatcacttg tcatattttt ttacattact   1440
atgttgttta tgtaaacaat atatttataa attatttttt cacaattata caactatat    1500 tattataatc atactaatta acatcactta actattttat actaaaagga aaaagaaaa    1560 taattatttc cttaccaatt ggggtaccta cctcctcctc gtactcctct tcctcctcat   1620
caataccagc atcctggtac tgctggtatt cggagacaag atcgttcatg ttggactcag   1680
cctcagtgaa ctccatctcg tccatacccct caccagtata ccaatgcaag aaagccttgc   1740
gtcggaacat ggcagtgaac tgctcaccaa cgcgcttgaa gagctcctgg atagaggtgg   1800
agtttccgat gaaggtcgaa gacatcgtaa gtcctcgggg agggatggca caagggctg    1860 tctggatatt gttgggaatc cattcaacga agtaagacga gttcttgctc tggacgttgc   1920
gcatctggtc ctcgacctcc ttcatagcga cacggccacg gaaaatggcc gagcaggtca   1980
ggtagcgacc gttgcggaag tccgaagcag ccatcatgtt cttggggtcg aacatctgtt   2040
gggtcaactc aggaacgctg acagcgcgga aagagtgagc accacggctg gtcagaggag   2100
caaagccgac catgaagaag tgtagacgag ggaaaggcac catgttgacg gcgagctttc   2160
ggaggtcgga gttcagctga ccggggaaac ggagacaggt ggtgacaccg gacataacag   2220
cagaaacaag gtagttgagg tcaccgtagg aggggttgga cagcttcagg gtgcgcatgc   2280
agatatcgta gagggcctcg ttatcgat                                       2308
```

```
<210> SEQ ID NO 5
<211> LENGTH: 16
<212> TYPE: DNA
<213> ORGANISM: artificial sequence
<220> FEATURE:
<223> OTHER INFORMATION: synthetic oligonucleotide

<400> SEQUENCE: 5
caagaccgac ctgtcc                                                       16

<210> SEQ ID NO 6
<211> LENGTH: 16
<212> TYPE: DNA
<213> ORGANISM: artificial sequence
<220> FEATURE:
<223> OTHER INFORMATION: synthetic oligonucleotide

<400> SEQUENCE: 6
ccatccgagt acgtgc                                                       16
```

```
<210> SEQ ID NO 7
<211> LENGTH: 16
<212> TYPE: DNA
<213> ORGANISM: artificial sequence
<220> FEATURE:
<223> OTHER INFORMATION: synthetic oligonucleotide

<400> SEQUENCE: 7
atcgataacg aggccc                                                     16

<210> SEQ ID NO 8
<211> LENGTH: 17
<212> TYPE: DNA
<213> ORGANISM: artificial sequence
<220> FEATURE:
<223> OTHER INFORMATION: synthetic oligonucleotide

<400> SEQUENCE: 8
acatcgtaag tcctcgg                                                    17

<210> SEQ ID NO 9
<211> LENGTH: 16
<212> TYPE: DNA
<213> ORGANISM: artificial sequence
<220> FEATURE:
<223> OTHER INFORMATION: synthetic oligonucleotide

<400> SEQUENCE: 9
gaaaacacgt ccctcg                                                     16

<210> SEQ ID NO 10
<211> LENGTH: 16
<212> TYPE: DNA
<213> ORGANISM: artificial sequence
<220> FEATURE:
<223> OTHER INFORMATION: synthetic oligonucleotide

<400> SEQUENCE: 10
tcttgccgta gtccac                                                     16

<210> SEQ ID NO 11
<211> LENGTH: 719
<212> TYPE: DNA
<213> ORGANISM: Magnaporthe grisea

<400> SEQUENCE: 11
tcggtcgtcg tggctgcaag gtcattgtca actacgccaa cagcaccgag tccgccgagg      60
aggtcgtcgc cgccatcaag aagaacggct ctgacgctgc ctgcgtcaag gccaacgttg     120
gtgtcgtcga ggacatcgtc aggatgttcg aggaggccgt caagatcttt ggcaagctcg     180
acatcgtttg ctccaacagc ggcgtcgtct ccttcggcca cgtcaaggac gtcacccctg     240
aggaatttga ccgtgtcttt accatcaaca cccgtggcca gttctttgtc gcccgcgagg     300
cctacaagca cctcgagatt ggtggtcgcc tgattctgat gggctccatc actggccagg     360
ccaaggctgt gcccaagcac gccgtctact caggatcaaa gggtgccatc gagacatttg     420
ctcgctgcat ggctatcgac atggccgaca agaagattac tgttaatgtg gttgctcctg     480
gtggtatcaa gaccgatatg taccatgcag tctgcaggga atacattcca aacggcgaga     540
atctctccaa cgaggaggtt gacgagtatg ccgcgagcgc ttggagccct ctacatcgtg     600
tgggcctgcc gatcgatatt gcccgtgtgg tctgctttct ggcctcgaac gatgcgggct     660
gggtcactgg gaaagtgatc ggtatcgacg gcggtgcttg catgtaaatg ggtgggggg     719
```

<210> SEQ ID NO 12
<211> LENGTH: 501
<212> TYPE: DNA
<213> ORGANISM: Magnaporthe grisea

<400> SEQUENCE: 12

```
atcccggtct tgataccacc aggagcaacc acattaacag taatcttctt gtcggccatg      60
tcgatagcca tgcagcgagc aaatgtctcg atggcaccct tgatcctga gtagacggcg     120
tgcttgggca cagccttggc ctggccagtg atggagccca tcagaatcag gcgaccacca     180
atctcgaggt gcttgtaggc ctcgcgggcg acaaagaact ggccacgggt gttgatggta     240
aagacacggt caaattcctc aggggtgacg tccttgacgt ggccgaagga gacgacgccg     300
ctgttggagc aaacgatgtc gagcttgcca agatcttga cggcctcctc gaacatcctg      360
acgatgtcct cgacgacacc aacgttggcc ttgacgcagg cagcgtcaga gccgttcttc     420
ttgatggcgg cgacgacctc ctcggcggac tcggtgctgt ggcgtagtt gacaatgacc      480
ttgcagccac gacgaccgag g                                              501
```

<210> SEQ ID NO 13
<211> LENGTH: 1220
<212> TYPE: DNA
<213> ORGANISM: artificial sequence
<220> FEATURE:
<223> OTHER INFORMATION: synthetic gene

<400> SEQUENCE: 13

```
tcggtcgtcg tggctgcaag gtcattgtca actacgccaa cagcaccgag tccgccgagg      60
aggtcgtcgc cgccatcaag aagaacggct ctgacgctgc ctgcgtcaag gccaacgttg     120
gtgtcgtcga ggacatcgtc aggatgttcg aggaggccgt caagatcttt ggcaagctcg     180
acatcgtttg ctccaacagc ggcgtcgtct ccttcggcca cgtcaaggac gtcacccctg     240
aggaatttga ccgtgtcttt accatcaaca cccgtggcca gttctttgtc gcccgcgagg     300
cctacaagca cctcgagatt ggtggtcgcc tgattctgat gggctccatc actggccagg     360
ccaaggctgt gcccaagcac gccgtctact caggatcaaa gggtgccatc gagacatttg     420
ctcgctgcat ggctatcgac atggccgaca agaagattac tgttaatgtg gttgctcctg     480
gtggtatcaa gaccgatatg taccatgcag tctgcaggga atacattcca aacggcgaga     540
atctctccaa cgaggaggtt gacgagtatg ccgcgagcgc ttggagccct ctacatcgtg      600
tgggcctgcc gatcgatatt gcccgtgtgg tctgctttct ggcctcgaac gatggcggct     660
gggtcactgg gaaagtgatc ggtatcgacg gcggtgcttg catgtaaatg ggtgggggga     720
tcccggtctt gataccacca ggagcaacca cattaacagt aatcttcttg tcggccatgt     780
cgatagccat gcagcgagca aatgtctcga tggcacccct tgatcctgag tagacggcgt     840
gcttgggcac agccttggcc tggccagtga tggagcccat cagaatcagg cgaccaccaa     900
tctcgaggtg cttgtaggcc tcgcgggcga caaagaactg gccacgggtg ttgatggtaa     960
agacacggtc aaattcctca ggggtgacgt ccttgacgtg gccgaaggag acgacgccgc    1020
tgttggagca aacgatgtcg agcttgccaa gatcttgac ggcctcctcg aacatcctga     1080
cgatgtcctc gacgacacca acgttggcct tgacgcaggc agcgtcagag ccgttcttct     1140
tgatggcggc gacgacctcc tcggcggact cggtgctgtt ggcgtagttg acaatgacct     1200
tgcagccacg acgaccgagg                                                1220
```

```
<210> SEQ ID NO 14
<211> LENGTH: 16
<212> TYPE: DNA
<213> ORGANISM: artificial sequence
<220> FEATURE:
<223> OTHER INFORMATION: synthetic oligonucleotide

<400> SEQUENCE: 14
cattgacttc acgcgg                                                   16

<210> SEQ ID NO 15
<211> LENGTH: 18
<212> TYPE: DNA
<213> ORGANISM: artificial sequence
<220> FEATURE:
<223> OTHER INFORMATION: synthetic oligonucleotide

<400> SEQUENCE: 15
gacactggat ttgacgtt                                                 18

<210> SEQ ID NO 16
<211> LENGTH: 17
<212> TYPE: DNA
<213> ORGANISM: artificial sequence
<220> FEATURE:
<223> OTHER INFORMATION: synthetic oligonucleotide

<400> SEQUENCE: 16
tgaccgtgtc tttacca                                                  17

<210> SEQ ID NO 17
<211> LENGTH: 18
<212> TYPE: DNA
<213> ORGANISM: artificial sequence
<220> FEATURE:
<223> OTHER INFORMATION: synthetic oligonucleotide

<400> SEQUENCE: 17
agcaaccaca ttaacagt                                                 18
```

METHOD FOR MODIFYING GENE EXPRESSION OF A PHYTOPATHOGENIC FUNGUS

CROSS REFERENCE TO RELATED APPLICATIONS

This application is a continuation-in-part application of International Patent Application No. PCT/FR2004/003312, filed on Dec. 20, 2004, published as WO 2005/071091, which claims priority to FR 0315228, filed Dec. 23, 2003, and to FR 0407373, filed Jul. 2, 2004, each of which are incorporated by reference herein in their entireties.

1. INTRODUCTION

The present invention relates to a system for controlling the development of fungi during a phytopathogenic attack. The system according to the invention consists in enabling the plant to express a construct for inhibiting the expression of a gene essential to the development or to the pathogenicity of the fungus. This system is commonly called RNA interference. The plants thus transformed constitute one of the aspects of the present invention.

2. BACKGROUND OF THE INVENTION

Plant diseases cause considerable yield losses; this results in economical losses for farmers, but also a large amount of nutritional damage for the local population living off their agriculture. Economically and ecologically, it is very advantageous to have plants resistant to their pathogens, and more particularly to their fungi in the absence of plant-protection products. To date, it has been possible to use various strategies:

Methods of traditional selection have been used to develop plants specifically resistant to certain pathogens. However, these methods are limited to the species that can be crossed and the introgression of characteristics of resistance to pathogens constitutes long and laborious work.

The use of an antisense RNA makes it possible to decrease the expression of an endogenous target gene (EP 240 208).

The use of a sense gene makes it possible to decrease the expression of an endogenous target gene; this technology is called cosuppression (EP 465 572).

The technology used in the context of the present invention is RNA interference or RNAi. RNAi has in particular proved that it is effective when double-stranded RNA (dsRNA) is injected into the nematode *Caenorhabditis elegans* (Fire et al. 1998, Nature 391: 806-811 and Montgomery et al., 1998, PNAS 95: 15502-15507, WO99/32619).

The expression in an organism of a sequence homologous to the gene of interest capable of inducing the formation of small double-stranded RNA makes it possible, very specifically, to extinguish this gene and to observe the phenotype that results therefrom (Xiao et al., 2003, Plant Mol Biol., 52(5): 957-66). The most striking example that illustrates this ability is that of insects fed with bacteria expressing small double-stranded RNAs corresponding to a gene expressed in the insects, which is thus inhibited (WO 01/37654).

The dsRNA triggers the specific degradation of a homologous RNA only in the region of identity with the dsRNA (Zamore et al., 2000, Cell, 101: 25-33, Tang et al., 2003 Gene Dev., 17(1): 49-63). The dsRNA is an RNA molecule which contains a double-stranded sequence of at least 25 base pairs (bp) including a sense strand and an antisense strand. The dsRNA molecules are also characterized by the very large degree of complementarity between the two complementary RNA strands. The dsRNA is degraded into RNA fragments of 19 to 25 nucleotides (siRNA) and the cleavage sites on the target RNA are evenly spaced apart by 19 to 25 nucleotides. The small siRNAs resulting therefrom exhibit a very high degree of identity with respect to the target RNA; however, mismatches of 3 to 4 nucleotides between the siRNA and the corresponding portion of the target RNA nevertheless make it possible for the system to operate (Tang et al., 2003, Genes Dev., 17:49-63). It has thus been suggested that these fragments of 19 to 25 nucleotides constitute RNA guides for recognition of the target (Zamore et al., 2000, Cell, 101:25-33). These small RNAs have also been detected in extracts prepared from Schneider 2 cells of *Drosophila melanogaster* which had been transfected with dsRNAs before cell lysis (Hammond et al., 2000, Nature 404: 293-296). The guiding role of the fragments of 19 to 25 nucleotides in the cleavage of the mRNAs is supported by the observation that these fragments of 19 to 25 nucleotides isolated from dsRNA are capable of being involved in the degradation of mRNA (Zamore et al., 2000, Cell, 101:25-33). Sizable homologous RNA molecules also accumulate in plant tissues which undergo the PTGS phenomenon (Post Transcriptional Gene Silencing, Hamilton and Baulcome, 1999, Science 286: 950-952). These small RNAs can regulate gene expression at three different levels:

transcription (TGS for Transcriptional Gene Silencing),
messenger RNA degradation (PTGS for Post Transcriptional Gene Silencing),
translation.

Regulation involving messenger RNA degradation appears to exist in all eukaryotes, whereas regulation at the transcriptional level has only been described in plants, drosophile and *C. elegans*. As regards the regulation of translation, it has been characterized in *C. elegans* and drosophile and appears also to exist in mammals (Hannon, 2002, Nature, 418 (6894): 244-51). In the literature, reference is made to RNAi, to PTGS, to cosuppression or to quelling (reserved for fungi) when referring to this phenomenon, depending on the organisms in which it is studied.

The introduction of dsRNA was carried out in plants in order to induce silencing of an endogenous target gene (Hamilton et al., 1998, Plant J, 15: 737-746, WO99/15682), to induce resistance to RNA viruses by means of the use of a transgene expressing a dsRNA having substantial identity with respect to the viral genes (Waterhouse et al., 1998, PNAS 95: 13959-13964, Pandolfini et al., 2003, Biotechnol., 25; 3(1): 7, WO98/36083, WO99/15682, U.S. Pat. No. 5,175, 102), but also to induce resistance to nematodes (Chuang and Meyerowitz, 2000, PNAS, 97: 4985-4990, WO01/96584) or alternatively to the bacterium *Agrobacterium* (WO00/26346, Escobar et al., 2001, Proc. Natl. Acad. Sci. USA., 98(23): 13437-13442).

In the case of the attack of a plant by a bacterium or by a virus, the mechanisms of interaction between the plant and the pathogen clearly involve nucleic acid transfers. In fact, in the case of *Agrobacterium tumefaciens*, the mechanisms of pathogenicity comprise two steps: the first corresponds to a horizontal gene transfer and to the integration of this or these gene(s) into the plant (this is transformation), the second corresponds to post-integration events that occur in the plant (this is tumorigenesis; Escobar et al., 2001, Proc. Natl. Acad. Sci. USA., 98(23): 13437-42) based on the use, by the plant, of the pathogen's genetic material. In the case of the infection of tobacco with the Plum Pox Virus (PPV), it is the transfer into the plant of the single-stranded RNA of the virus which allows the synthesis of the capsid proteins and of the polymerases required for the propagation of the infection (Pandolfini et al., 2003). There is therefore a link and very elaborate exchanges at the genetic level between the plant and its pathogen, and the siRNAs are transferred during its exchanges. The mechanisms of infection of a plant by a phytopathogenic fungus do not, for their part, involve any gene transfer.

3. SUMMARY OF THE INVENTION

A subject of the present invention is the creation of a construct and the use thereof in plants or cells genetically modified in order to make them resistant to pathogenic fungi. The technology used is based on the mechanism of RNA interference. These plants have the advantage of not producing proteins, and the risks of allergic problems are considerably reduced: the only elements overexpressed being RNAs. Furthermore, the mechanism of interference RNA is an exponential and self-replicating system, which means that it is sufficient to induce it in order for it to be maintained in the organism.

One of the subjects of the present invention concerns a method of producing a plant resistant to a phytopathogenic fungus, comprising the following steps:
a) introducing into a plant cell a construct comprising:
   a promoter regulatory sequence that is functional in plant cells,
   a DNA sequence which, when it is transcribed, generates an RNA molecule comprising at least two sequences: sense and antisense at least partially complementary, said sense sequence comprising a sequence essentially homologous to a gene essential to the fungus or to its phytopathogenicity, said antisense sequence comprising a sequence essentially homologous to the sequence complementary to said essential gene,
   a terminator regulatory sequence,
b) placing the transformed cells in culture under conditions that allow the transcription of the construct,
c) selecting the transformed cells,
d) regenerating plants from the transformed cells.

Another subject of the present invention concerns a method of producing a plant resistant to a phytopathogenic fungus, comprising the following steps:
a) introducing into a plant a construct comprising:
   a promoter regulatory sequence that is functional in plant cells,
   a DNA sequence which, when it is transcribed, generates an RNA molecule comprising at least two sequences: sense and antisense at least partially complementary, said sense sequence comprising a sequence essentially homologous to a gene essential to the fungus or to its phytopathogenicity, said antisense sequence comprising a sequence essentially homologous to the sequence complementary to said essential gene,
   a terminator regulatory sequence,
b) placing the transformed plants in culture under conditions that allow the transcription of the construct,
c) selecting the transformed plants.

Another subject of the present invention concerns a method of producing a plant cell resistant to a phytopathogenic fungus, comprising the following steps:
a) introducing into a plant cell a construct comprising:
   a promoter regulatory sequence that is functional in plant cells,
   a DNA sequence which, when it is transcribed, generates an RNA molecule comprising at least two sequences: sense and antisense at least partially complementary, said sense sequence comprising a sequence essentially homologous to a gene essential to the fungus or to its phytopathogenicity, said antisense sequence comprising a sequence essentially homologous to the sequence complementary to said essential gene,
   a terminator regulatory sequence,
b) selecting the transformed cells,
c) placing the transformed cells in culture under conditions that allow the transcription of the construct.

The invention also concerns a plant resistant to a phytopathogenic fungus, comprising a construct characterized in that it comprises:
   a promoter regulatory sequence that is functional in plant cells,
   a DNA sequence which, when it is transcribed, generates an RNA molecule comprising at least two sequences: sense and antisense at least partially complementary, said sense sequence comprising a sequence essentially homologous to a gene essential to the fungus or to its phytopathogenicity, said antisense sequence comprising a sequence essentially homologous to the sequence complementary to said essential gene,
   a terminator regulatory sequence.

The plant cells resistant to a phytopathogenic fungus comprising a construct characterized in that it comprises:
   a promoter regulatory sequence that is functional in plant cells,
   a DNA sequence which, when it is transcribed, generates an RNA molecule comprising at least two sequences: sense and antisense at least partially complementary, said sense sequence comprising a sequence essentially homologous to a gene essential to the fungus or to its phytopathogenicity, said antisense sequence comprising a sequence essentially homologous to the sequence complementary to said essential gene,
   a terminator regulatory sequence,
are another subject of the present invention.

Another aspect of the present invention concerns the use of a construct for creating a plant cell or a plant resistant to a fungus, said construct comprising a promoter regulatory sequence that is functional in plant cells, a DNA sequence which, when it is transcribed, generates an RNA molecule comprising at least two sequences: sense and antisense at least partially complementary, said sense sequence comprising a sequence essentially homologous to a gene essential to the fungus or to its phytopathogenicity, said antisense sequence comprising a sequence essentially homologous to the sequence complementary to said essential gene, and a terminator regulatory sequence.

A subject of the invention is also a method for identifying a gene essential to the development or to the pathogenicity of a phytopathogenic fungus, comprising the following steps:
a) transforming a plant cell or a plant with a construct comprising:
   a promoter regulatory sequence that is functional in plant cells,
   a DNA sequence which, when it is transcribed, generates an RNA molecule comprising at least two sequences: sense and antisense at least partially complementary, said sense sequence comprising a sequence essentially homologous to a gene supposedly essential to the fungus or to its phytopathogenicity, said antisense sequence comprising a sequence essentially homologous to the sequence complementary to said supposed essential gene, a terminator regulatory sequence, b) bringing the cells or the plants thus transformed into contact with the phytopathogenic fungus,
c) studying the resulting phenotype,
d) characterizing the gene corresponding to the sequence of nucleotides thus inserted.

A method for inhibiting the expression of a fungal gene, comprising the following steps:

a) transforming a plant cell or a plant with a construct comprising:

a promoter regulatory sequence that is functional in plant cells, a DNA sequence which, when it is transcribed, generates an RNA molecule comprising at least two sequences: sense and antisense at least partially complementary, said sense sequence comprising a sequence essentially homologous to a gene essential to the fungus or to its phytopathogenicity, said antisense sequence comprising a sequence essentially homologous to the sequence complementary to said essential gene, a terminator regulatory sequence, b) selecting,
c) placing the cells thus transformed in culture under conditions that allow the transcription of said construct,
d) bringing the cells into contact with the fungus, constitutes yet another aspect of the invention.

The invention also concerns a method for reducing the expression of a fungal gene, comprising the following steps:

a) transforming a plant cell or a plant with a construct comprising:

a promoter regulatory sequence that is functional in plant cells, a DNA sequence which, when it is transcribed, generates an RNA molecule comprising at least two sequences: sense and antisense at least partially complementary, said sense sequence comprising a sequence essentially homologous to a gene essential to the fungus or to its phytopathogenicity, said antisense sequence comprising a sequence essentially homologous to the sequence complementary to said essential gene, a terminator regulatory sequence, b) selecting,
c) placing the cells thus transformed in culture under conditions that allow the transcription of said construct,
d) bringing the cells into contact with the fungus.

4. BRIEF DESCRIPTION OF THE FIGURES

FIG. 1 depicts a promoter regulatory sequence that is functional in plant cells, operably linked to a nucleotide sequence in the sense orientation of a target gene, followed by an intron and by a nucleotide sequence in the antisense orientation of this same gene. A terminator regulatory sequence is at the end of the sense/intron/antisense construct. The sequence cloned in the sense and antisense orientation is that whose expression in the pathogen it is intended to inhibit. The dsRNA product of the construct is processed by dicer to form siRNA, or interfering RNA.

FIG. 2 represents a promoter regulatory sequence that is functional in plant cells, which is in front of the sense sequence of the gene, followed by the partial antisense sequence of this same gene. A terminator regulatory sequence is at the end of the sense/antisense construct. The dsRNA product of the construct is processed by dicer to form siRNA, or interfering RNA.

FIG. 3 shows the position of the *Cercospora nicotianae* tubulin primers on the DNA and RNA sequences comprising the sense-intron-antisense assembly as defined by the sequence identifier SEQ ID No. 4. The dashed lines represent diagrammatically the primers with which the quantitative PCR (qPCR) is carried out after the reverse transcription (RT).

FIG. 4A-F depicts different types/stages of progression of a fungal infection. (A) Type 1 corresponds to the visualization of very slight, barely perceptible, marks on the leaf. (B) Type 2 corresponds to clear, but very few, marks on the leaf. (C) Type 3 corresponds to clear and numerous marks on the leaf. (D) Type 4 corresponds to very clear and very numerous marks with the presence of large marks. Type 5 corresponds either to complete rotting of the leaf (E), or to numerous very large marks (F).

FIG. 5 represents the intensity of the symptoms noted for each event.

FIG. 6 represents the percentage of contaminated foliar surface for each event.

FIG. 7 presents the intensity of the symptoms noted for each event.

5. DETAILED DESCRIPTION OF THE INVENTION

According to the invention, the term "promoter regulatory sequence" is intended to mean any promoter regulatory sequence of a gene that is naturally expressed in plants, in particular a promoter that is expressed especially in the leaves of plants, for instance promoters referred to as constitutive of bacterial, viral or plant origin, or else promoters referred to as light-dependent, such as that of a plant ribulose-biscarboxylase/oxygenase (RuBisCO) small subunit gene, or any known suitable promoter that can be used. Among the promoters of plant origin, mention will be made of the histone promoters as described in application EP 0 507 698, or the rice actin promoter (U.S. Pat. No. 5,641,876). Among the promoters of a plant virus gene, mention will be made of that of the cauliflower mosaic virus (CaMV 19S or 35S) or of the cassava vein mosaic virus (CsVMV: WO97/48819) or the circovirus promoter (AU 689 311). Use may also be made of a promoter regulatory sequence specific for particular regions or tissues of plants, and more particularly seed-specific promoters (Datla, R. et al., 1997, Biotechnology Ann. Rev., 3, 269-296), especially the napin (EP 255 378), phaseolin, glutenin, helianthinin (WO 92/17580), albumin (WO 98/45460) and oleosin (WO 98/45461) promoters. An inducible promoter can also be used, it can be advantageously chosen from the promoters of phenylalanine ammonia lyase (PAL), of HMG-CoA reductase (HMG), of chitinases, of glucanases, of proteinase inhibitors (PI), of genes of the PR1 family, of nopaline synthase (nos) or of the vspB gene (U.S. Pat. No. 5,670,349), the HMG2 promoter (U.S. Pat. No. 5,670,349), the apple beta-galactosidase (ABG1) promoter or the apple amino cyclopropane carboxylate synthase (ACC synthase) promoter (WO 98/45445).

The term "terminator regulatory sequence" is intended to mean any sequence that is functional in plant cells or plants, also comprising polyadenylation sequences, whether they are of bacterial origin, for instance the nos or ocs terminator of *Agrobacterium tumefaciens*, of viral origin, for instance the CaMV 35S terminator, or else of plant origin, for instance a histone terminator as described in application EP 0 633 317.

The selection step for identifying the transformed cells and/or plants having integrated the construct according to the invention can be carried out by virtue of the presence of a selectable gene present in the construct according to the invention or in the plasmid used for the transformation of the cells or of the plants and comprising said construct. The selectable gene may be in the form of a chimeric gene comprising the following elements, functionally linked in the direction of transcription: a promoter regulatory sequence that is functional in plant cells, a sequence encoding a selectable marker, and a terminator regulatory sequence that is functional in plant cells.

Among the selectable markers that can be used, mention may be made of markers containing genes for resistance to antibiotics, such as, for example, that of the hygromycin phosphotransferase gene (Gritz et al., 1983, Gene 25: 179-188), of the neomycin phosphotransferase II gene inducing resistance to kanamycin (Wirtz et al., 1987, DNA, 6(3): 245-253), or of the aminoglycoside 3"-adenyltransferase gene, but also markers containing genes for tolerance to herbicides, such as the bar gene (White et al., NAR 18: 1062, 1990) for tolerance to bialaphos, the EPSPS gene (U.S. Pat. No. 5,188,642) for tolerance to glyphosate or else the HPPD gene (WO 96/38567) for tolerance to isoxazoles. Mention may also be made of genes encoding readily unidentifiable enzymes, such as the GUS enzyme, or genes encoding pigments or enzymes regulating pigment production in the transformed cells. Such selectable marker genes are in particular described in patent applications WO 91/02071, WO 95/06128, WO 96/38567, and WO 97/04103.

Preferably, the nucleotide sequence of the gene essential to the fungus or to its pathogenicity (target gene) corresponds to a region which is transcribed, and more particularly which is transcribed and translated.

The length of the sense nucleotide sequence has a minimum size of 19 nucleotides.

The sense sequence comprises a sequence essentially homologous to a gene essential to the fungus or to its pathogenicity. In fact, and preferably, the sense nucleotide sequence and the nucleotide sequence of the fungal target gene exhibit a degree of identity of at least 50% to 70%. Entirely preferably, the degree of identity is at least 75%, at least 80%, at least 85%, at least 90%, at least 95%, and entirely preferably, the degree of identity is 100%.

However, it is necessary for the sense nucleotide sequence to always comprise a sequence of approximately 19 nucleotides, particularly of 20 nucleotides, and more particularly of 25 nucleotides, exhibiting at least 80% identity with the corresponding portion of the target gene, at least 85% identity with the corresponding portion of the target gene, at least 90% identity with the corresponding portion of the target gene, at least 95% identity with the corresponding portion of the target gene, and entirely preferably 100% identity.

In one of the aspects of the invention, the sense and antisense sequences have identical sizes. According to another aspect of the invention, the size of the sense sequence is greater than that of the antisense sequence. By way of example, the size of the sense sequence can be about 200 nucleotides greater than the size of the antisense sequence. In another aspect of the invention, the size of the antisense sequence is greater than that of the sense sequence.

The antisense sequence comprises a sequence essentially homologous to the sequence complementary to the gene essential to the fungus or to its pathogenicity. In fact, and preferably, the antisense nucleotide sequence and the sequence complementary to the fungal target gene exhibit a degree of identity of at least 50% to 70%. Entirely preferably, the degree of identity is at least 75%, at least 80%, at least 85%, at least 90%, at least 95%, and entirely preferably, the degree of identity is 100%.

However, it is necessary for the antisense nucleotide sequence to always comprise a sequence of approximately 19 nucleotides, particularly of 20 nucleotides, and more particularly of 25 nucleotides, exhibiting at least 80% identity with the corresponding portion of the target gene, at least 85% identity with the corresponding portion of the target gene, at least 90% identity with the corresponding portion of the target gene, at least 95% identity with the corresponding portion of the target gene, and entirely preferably 100% identity.

Molecular hybridization is a pairing reaction which takes place between complementary strands of polynucleotides exhibiting a certain degree of identity between their nucleotide sequences. The greater the sequence identity between the polynucleotides, the more possible and easier the hybridization between said polynucleotides, and the greater the probability that these polynucleotides encode proteins with equivalent properties.

The degree of identity between two homologous polynucleotides is obtained by comparison of their sequences and is generally expressed by means of a percentage of nucleotides that are identical between these sequences. This degree of identity is measured over a given sequence length, the shortest of the sequences compared determining the length of sequence over which the degree of identity of the homologous sequences is measured. The invention therefore covers polynucleotides exhibiting one or more sequence modifications with respect to the other and being homologous to the gene essential to the fungus or to its pathogenicity.

The DNA sequence according to the invention can have two aspects; in the first, it comprises two nucleotide sequences, which are sense and antisense, separated by an intron that does not exhibit any homology with the fungal gene. FIG. 1 describes a promoter regulatory sequence that is functional in plant cells, which is in front of the nucleotide sequence in the sense orientation of the gene, followed by an intron and by the nucleotide sequence in the antisense orientation of this same gene. A terminator regulatory sequence is at the end of the sense/intron/antisense construct. The sequence cloned in the sense and antisense orientation is that whose expression in the pathogen it is intended to inhibit. The transcription of this DNA sequence ("DNA" in the figure) thus gives a large single-stranded RNA ("mRNA" in the figure) corresponding to the sense/intron/antisense construct. This long RNA transcript can be detected by RT-PCR. Since the sense and antisense sequences are homologous, they will pair, and the intron which separates them plays the role of a loop for folding. A dsRNA is then obtained ("dsRNA" in the figure) over all the homologous regions. The dsRNA is subsequently specifically degraded by an enzymatic complex called "DICER". The degradation of the dsRNAs then forms siRNAs ("siRNA" in the figure), small double-stranded RNAs having a size of between 19 and 25 bases. These are then the siRNAs which, by pairing with the transcribed RNAs derived from the target gene will lead to their degradation via the plant's enzymatic machinery.

In the second aspect, the DNA sequence comprises two nucleotide sequences, which are sense and antisense, of different sizes, the loop structure corresponding to the part of the nucleotide sequence that does not exhibit any homology with the other nucleotide sequence. FIG. 2 represents a promoter regulatory sequence that is functional in plant cells, which is in front of the sense sequence of the gene, followed by the partial antisense sequence of this same gene. A terminator regulatory sequence is at the end of the sense/antisense construct. The nucleotide sequence cloned in the sense orientation is essentially homologous to the sequence of the target gene whose expression it is intended to inhibit. The antisense nucleotide sequence is essentially homologous to the complementary strand of the sequence of said target gene. The transcription of this DNA sequence ("DNA" in the figure) thus gives a large single-stranded RNA ("mRNA" in the figure) corresponding to the sense/antisense construct (this long RNA transcript can be detected by RT-PCR) The homologous sense/antisense sequences are paired. A dsRNA is then obtained ("dsRNA" in the figure) over all the homologous regions. The dsRNA is subsequently specifically degraded by an enzymatic complex called "DICER". The degradation of the dsRNAs then forms siRNAs ("siRNA" in the figure), small doubled-stranded RNAs having a size of between 19 and 25 bases. These are then the siRNAs which, by pairing with the target RNAs, will lead to their degradation via the plant's enzymatic machinery.

The nucleotide sequences according to the present invention can be complementary to a gene essential to the fungus or to its pathogenicity.

According to the invention, the expression "gene essential to the fungus" is intended to mean a gene, the inhibition of which by a fungicidal molecule or the mutation thereof leads to the death of the fungus or an arrest of its development. By way of example, mention may be made of the following genes:

gene encoding beta-tubulin (Katiyar et al., 1994, Antimicrob. Agents Chemother., 38(9): 2086-90), acetohydroxyacid isomerase (ilv5) involved in the branched-chain amino acid biosynthetic pathway (WO 03/022056), C14-demethylase (erg11) or C24-methyltransferase (erg6) involved in the ergosterol synthetic pathway (Barrett and Dixon, 1995, Acta Biochem. Pol., 42(4): 465-479), inositol phosphoceramide synthase (aur1) involved in the transfer of inositol phosphoceramide onto ceramide in the sphingolipid biosynthetic pathway (Nagiec et al., 1997, J. Biol. Chem., 272(15): 9809-9817) and inositol phosphoryltransferase (ipt1), glucan synthase and chitin synthase (Kang et al., 2001, Pest. Mana. Sci., 57(6): 491-500, Binks et al., 1993, J. Gen. Microbiol., 139(6): 1371-1377), ribosomal factors (ef2 and ef3, Belfiel and Tuite, 1993, Mol. Microbiol., 9(3): 411-418), met4 and met30 (Aoki et al., 1996, Antimicrob. Agents Chemother, 40(1): 127-132).

Additional examples of genes encompassed by the expression "gene essential to the fungus" can be found in Table 1.

In one embodiment of the invention, the plants or plant cells comprise a complementary DNA sequence of a gene essential to the fungus, said essential gene being represented by the sequence identifier SEQ ID No. 4.

The invention also relates to a method of producing a tobacco cell resistant to the fungus *Cercospora nicotianae*, by introducing a construct comprising a DNA sequence represented by the sequence identifier SEQ ID No. 4.

According to the invention, the expression "gene essential to the pathogenicity of the fungus" is intended to mean a gene, the inhibition of which is not lethal for the fungus but inhibits its pathogenic capacity. By way of example, mention may be made of the following genes:

763 of *Magnaporthe grisea* (WO 01/75115), gene encoding polygalacturonase (Bonnin et al., 2001, Biochem. Biophys. Acta, 1526(3): 301-309), tri5 of *Fusarium graminearum*, involved in the trichothecene biosynthetic pathway (Kimura et al., 2003, FEBS, 539(1-3): 105-110), fum5 of *Fusarium monoliforme*, involved in the biosynthetic pathway for toxins of this fungus (Proctor et al., 1999, Fungal Genet. Biol., 27(1): 100-112, Proctor et al., 2003, Fungal Genet. Biol., 38(2): 237-249), buf of *Magnoporthe grisea*, involved in the melanin biosynthetic pathway (Kawamura et al., 1997, Mol. Plant Microbe Interact, 10(4): 446-453).

In another embodiment of the invention, the plants or plant cells comprise a complementary DNA sequence of a gene essential to the pathogenicity of the fungus, said gene being represented by the sequence identifier SEQ ID No. 13.

The methods of the present invention may be utilized to target genes in a wide variety of fungi that infect plants. Plants which can be afflicted by fungal disease include, but are not limited to: African Daisy (*Gerbera jamesonii* H. Bolus ex J. D. Hook), African Violet (*Saintpaulia ionantha* Wendl.), Alfalfa (*Medicago sativa* L.), Almond (*Prunus dulcis* (Mill.) Webb), Anemone (*Anemone coronaria* L.), Apple (*Malus× domestica* Borkh.), Apricot (*Prunus armeniaca* L.), Asparagus (*Asparagus officinalis*), Avocado (*Persea americana* Miller), Azalea (*Rhododendron* spp.), Banana and Plantain (*Musa* spp.), Barley (*Hordeum vulgare* L.) Beet (*Beta vulgaris* L.), Beilfiower (*Campanula carpatica* Jacq.), Black Walnut (*Juglans nigra* L.), Bleeding Heart (*Clerodendrum thomsoniae* Balf.), Butterfly Flower, Poorman's Orchid (*Schizanthus×wisetonensis* hort.), Cacao (*Theobroma cacao* L.), Caneberries (*Rubus* spp.), Carnation (*Dianthus caryophylium* L.), Carrot (*Daucus carota* L. subsp. *sativus* (Hoffm.) (Arcang.), Cassava (*Manihot esulenta* Crantz), Cattleya Lindl. spp., Chickpea (*Cicer arietinum* L.), Cinerama (*Pericallis×hybrida* R. Nordenstam [*Senecio×hybridus* (Wilid.) Regel], Citrus (*Citrus* spp.), Coconut Palm (*Cocos nucifera* L.), Coffee (*Coffea arabica* L., *Coffea canephora* Pierre ex Froehner), Corn or Maize (*Zea mays* L.), Cotton (*Gossypium* spp.), Crucifers (*Brassica* and *Raphanus* spp.), Cucurbits (*Citrullus* spp., *Cucumis* spp., *Cucurbita* spp., and others), Cyclamen (*Cyclamen persicum* Mill.), Dahlia (*Dahlia* sp.), Date Palm (*Phoenix dactylifera* L.), Douglas-fir (*Pseudotsuga menziezii* [Mirb.] Franco), Elm (*Ulmus* spp.), English (Persian) Walnut (*Juglans regia* L.), Flax (*Linum usitatissimum* L. and other *Linum* spp.), Foliage Plants (House plants), Fuchsia (*Fuchsia×hybrida* Hort. ex Vilm), Geranium (Pelargonium), Grape (*Vitis* spp.), Hazelnut (*Corylus avellana* L. & *Corylus* spp.), Hemp (*Cannabis sativa* L.), Holiday Cacti (*Schlumbergera truncata* (Haw.) Moran), Hop (*Humulus lupulus* L.), Hydrangea (*Hydrangea macrophylla* (Thunb.) Ser., Impatiens (*Impatiens wallerana*) and New Guinea impatiens (*Impatiens* hybrids), Jerusalem Cherry (*Solanum pseudocapsicum* L.), Kalanchoe (*Kalanchoe blossfeldiana* Poelln.), Lettuce (*Lactuca sativa* L.), Lentil (*Lens culinaris* Medik.), Lisianthus (*Eustoma grandiflorum* (Raf.) Shinn), Mango (*Mangifera indica* L.), Mimulus, Monkey-Flower (*Mimulus×hybridus* hort. ex Siebert & Voss), Mint (*Mentha piperita* L., *M. cardiaca* Baker, *M. spicata* L. and *M. arvensis* L.), Mustard (*Brassica juncea* (L.) Czernj. & J. M. Coulter var. *crispifolia* L. H. Bailey and *B. nigra* (L.) W. Koch), Oats (*Avena sativa* L.), Papaya (*Carica papaya* L.), Pea (*Pisum sativum* L.), Peach and Nectarine (Peach: *Prunus persica* (L.) Batsch; Nectarine: *P. persica* var. *nucipersica* (Suckow) C. K. Schneid.), Peanut (*Arachis hypogaea* L.), Pear (*Pyrus communis* L.), Pearl Millet (*Pennisetum glaucum* (L.) R. Br.), Pecan (*Carya illinoinensis* (Wang.) Koch.), Pepper (*Capsicurii* spp.), Persian Violet (*Exacum affine*), Pigeonpea (*Cajanus cajan* (L.) Millsp.), Pineapple (*Ananas comosus (L.) Merr.), Pistachio (*Pistacia vera* L.), Pocketbook Plant (*Calceolaria crenatiflora* Cav.), Poinsettia (*Euphorbia pulcherrima* Willd. ex Klotzsch), Potato (*Solanum tuberosum* L.), Primulas: English primrose *Primula vulgaris* Huds. (*P. acaulis*), Polyanthus Primula Pruhonicensis hybrids, Fairy primrose *P. malacoides* Franch., German primrose *P. obconica* Hance, Chinese primrose *P. sinensis* Sabine ex Lindl., Rapeseed=Canola (*B. napus* L. and *Brassica rapa* L. (=*B. campestris* L.)), Red Clover (*Trifolium pratense* L.), Rhododendron (*Rhododendron* spp.), Rice (Oryza sativa L.), Rose (*Rosa* spp.), Rye (*Secale cereale* L.), Safflower (*Carthamus tinctorius* L.), Sapphire Flower (*Browallia speciosa* Hook.), Sorghum (*Sorghum bicolor* (L.) Moench), Soybeans (*Glycine max* (L.) Merrill), Spinach (*Spinacia oleracea* L.), Strawberry (*Fragaria×ananassa* Duch.), Sugarcane (*Saccharum* spp. hybrids), Sunflower (*Helianthus annuus* L.) and Jerusalem Artichoke (*H. tuberosus* L.), Sweetgum (*Liquidambar* spp.), Sweetpotato (*Ipomoea batatas* (L.) Lam.), Sycamore (*Platanus* spp.), Tea (*Camellia sinesis* (L.) 0. Kuntze), Tobacco (*Nicotiana tabacum* L.), Tomato (*Lycopersicon esculentum* Mill.), Verbena (*Verbena×hybrida* Groenl. & Ruempi.), Wheat (*Triticum* spp. L.), Wild Rice, Cultivated (*Zizania palustris* L.). Table 2 provides a list of common diseases which infect various types of plants, as well as identified sources of the disease. The prior list and Table 2 were compiled from data found at the International Society for Molecular Plant-Microbe Interactions Based upon the methods disclosed herein, a person of ordinary skill in the art will be capable of utilizing the methods described above to target specific genes essential to a fungus or its pathogenicity in the fungus responsible for a particular fungal diseases outlined in Table 2. For example, the beta-tubulin gene of a fungus described in Table 2 may be targeted. A person of ordinary skill in the art will also be capable of utilizing analogous methods to treat fungal diseases for the plants listed herein.

The invention also relates to a method of producing a rice cell resistant to the fungus *Magnoporthe grisea*, by introducing a construct comprising a DNA sequence represented by the sequence identifier SEQ ID No. 13.

The plants and the cells transformed according to the invention can be monocotyledons or dicotyledons. Preferably, these plants are plants of agronomic interest.

The plant cells and the plants of the present invention can be monocotyledons such as wheat, maize or rice.

A particular embodiment of the present invention corresponds to a rice plant resistant to *Magnaporthe grisea*, comprising a DNA sequence represented by the sequence identifier SEQ ID No. 13.

The plant cells and the plants of the present invention can be dicotyledons such as rapeseed, soybean, cotton or tobacco.

A particular embodiment of the present invention corresponds to a tobacco plant resistant to *Cercospora nicotianae*, comprising a DNA sequence represented by the sequence identifier SEQ ID No. 4.

Said plant can be obtained by regeneration of the transformed cells according to the invention.

To obtain the cells or plants according to the invention, those skilled in the art can use one of the numerous known methods of transformation.

One of these methods consists in bringing the cells or tissues of the host organisms to be transformed into contact with polyethylene glycol (PEG) and the vectors of the invention (Chang and Cohen, 1979, Mol. Gen. Genet. 168(1), 111-115; Mercenier and Chassy, 1988, Biochimie 70(4), 503-517). Electroporation is another method, which consists in subjecting the cells or tissues to be transformed and the vectors of the invention to an electric field (Andreason and Evans, 1988, Biotechniques 6(7), 650-660; Shigekawa and Dower, 1989, Aust. J. Biotechnol. 3(1), 56-62). Another method consists in directly injecting the vectors into the cells or the tissues by microinjection (Gordon and Ruddle, 1985, Gene 33(2), 121-136). Advantageously, the "biolistic" method may be used. It consists in bombarding cells or tissues with particles onto which the vectors of the invention are adsorbed (Bruce et al., 1989, Proc. Natl. Acad. Sci. USA 86(24), 9692-9696; Klein et al., 1992, Biotechnology 10(3), 286-291; U.S. Pat. No. 4,945,050). Preferably, the transformation of plant cells or tissues can be carried out using bacteria of the *Agrobacterium* genus, preferably by infection of the cells or tissues of said plants with *A. tumefaciens* (Knopf, 1979, Subcell. Biochem. 6, 143-173; Shaw et al., 1983, Gene 23(3): 315-330) or *A. rhizogenes* (Bevan and Chilton, 1982, Annu. Rev. Genet. 16: 357-384; Tepfer and Casse-Delbart, 1987, Microbiol. Sci. 4(1), 24-28). Preferably, the transformation of plant cells or tissues with *Agrobacterium tumefaciens* is carried out according to the protocol described by Hiei et al., (1994, Plant J. 6(2): 271-282). Those skilled in the art will choose the appropriate method according to the nature of the host organisms to be transformed.

The plants according to the invention contain transformed plant cells as defined above. In particular, the transformed plants can be obtained by regeneration of the transformed plant cells described above. The regeneration is obtained by any appropriate method, which depends on the nature of the species.

The invention also comprises parts of these plants, and the progeny of these plants. The term "part of these plants" is intended to mean any organ of these plants, whether above ground or below ground. The organs above ground are the stems, the leaves and the flowers comprising the male and female reproductive organs. The organs below ground are mainly the roots, but they may also be tubers. The term "progeny" is intended to mean mainly the seeds containing the embryos derived from the reproduction of these plants with one another. By extension, the term "progeny" applies to all the seeds formed at each new generation derived from crosses between the transformed plants according to the invention. Progeny and seeds can also be obtained by vegetative multiplication of said transformed plants. The seeds according to the invention can be coated with an agrochemical composition comprising at least one active product having an activity selected from fungicidal, herbicidal, insecticidal, nematicidal, bactericidal or virucidal activities.

The various aspects of the invention will be understood more fully by means of the experimental examples below.

All the methods or operations described below are given by way of example and correspond to a choice, made among the various methods available for achieving the same result. This choice has no effect on the quality of the result, and, consequently, any appropriate method can be used by those skilled in the art to achieve the same result. In particular, and unless otherwise specified in the examples, all the recombinant DNA techniques employed are carried out according to the standard protocols described in Sambrook and Russel (2001, Molecular cloning: A laboratory manual, Third edition, Cold Spring Harbor Laboratory Press, NY) in Ausubel et al. (1994, Current Protocols in Molecular Biology, Current protocols, USA, Volumes 1 and 2), and in Brown (1998, Molecular Biology LabFax, Second edition, Academic Press, UK). Standard materials and methods for plant molecular biology are described in Croy R. D. D. (1993, Plant Molecular Biology LabFax, BIOS Scientific Publications Ltd (UK) and Blackwell Scientific Publications (UK)). Standard materials and methods for PCR (Polymerase Chain Reaction) are also described in Dieffenbach and Dveksler (1995, PCR Primer: A laboratory manual, Cold Spring Harbor Laboratory Press, NY) and in McPherson et al. (2000, PCR—Basics: From background to bench, First edition, Springer Verlag, Germany).

EXAMPLES

Example 1

Creation of a Tobacco Plant Resistant to *Cercospora nicotianae*

*Cercospora nicotianae* is a pathogen of tobacco (*Nicotiana tabacum*). The target gene chosen in *Cercospora nicotianae* is the gene encoding beta-tubulin. Tubules are dynamic structures present in all cell types. In cells which have the ability to divide, the microtubules form the basis of the formation of the mitotic spindle; for the other cell types, they constitute a cytoplasmic network essential for the organization of the nucleus and of the organelles in the cytoplasmic space. Microtubules are heterodimers of alpha- and beta-tubulin. Beta-tubulin is a protein that is essential for the pathogen and is in particular the target for benzimidazoles (Katiyar et al., 1994, Antimicrob. Agents Chemother, 38(9): 2086-2090).

1.—Construct Used to Transform Tobacco Cells

The construct used to transform tobacco is the plasmid called pPAF 115; it comprises the following selectable markers: a gene for resistance to kanamycin under the control of the nos promoter, a gene for resistance to spectinomycin (aadA) under the control of a bacterial promoter. The CaMV 35S promoter allows transcription of the DNA sequence comprising part of the sense sequence of *Cercospora nicotianae* beta-tubulin, represented by the sequence identifier SEQ ID No. 1, itself followed by an intron represented by the sequence identifier SEQ ID No. 2 and by the antisense sequence of this same beta-tubulin, represented by the sequence identifier SEQ ID No. 3. An ocs terminator is downstream of the sense-intron-antisense assembly. This assembly is represented by the sequence identifier SEQ ID No. 4.

The *Nicotiana tabacum* variety Petit Havana is transformed with this vector pPAF 115.

2.—Transformation of Tobacco Foliar Tissues Using the Solution of *Agrobacterium* Transformed with the Plasmid pPAF115

The solution of *Agrobacterium* (OD=1) is washed in 10 mM MgSO$_4$. Disks are cut out of wild-type tobacco leaves and are disinfected for 10 min in 75% ethanol and then incubated for 5 min in the solution of *Agrobacterium*. They are then sponged, and placed with the lower face against a Petri dish containing MS 0.05-2 agar (Murashige & Skoog M5519, 30 g/l sucrose, 0.05 ppm ANA, 2 ppm BAP, 7 g/l phytagar, pH=5.7) for a culture of three days. The foliar disks are transferred onto MS 0.05-2 dishes in the presence of spectinomycin and kanamycin for two to four weeks. The foliar disks are then placed on MS 0-0 medium (Murashige & Skoog M5519, 30 g/l sucrose, 7 g/l phytagar, pH=5.7) also containing the antibiotics for seven to ten days. The tobacco shoots derived from the disks are isolated and rooted on MS ½-½ agar dishes (½ Murashige & Skoog, 15 g/l sucrose, 7 g/l phytagar, pH=5.7) containing the antibiotics. Once the first two leaves have appeared, the shoots are placed in earth in order for the plants to develop.

3.—Molecular Analyses Carried Out on the Transgenic Tobacco

Three different events were obtained.

3.1.—PCR

First PCR experiments are carried out on the genomic DNA of the various events in order to determine whether the latter contain the construct according to the invention. Primers for detecting the kanamycin gene and also the *Cercospora*-specific tubulin were used.

|  | Event | | | |
| --- | --- | --- | --- | --- |
|  | 14 | 15 | 19 | WT |
| Kanamycin | + | + | + | − |
| Tubulin | + | + | + | − |

WT: wild-type, nontransformed plant.

The sequences of the primers used are as follows:

```
Kanamycin:
direct:  5'-CAA GAC CGA CCT GTC C-3'   (SEQ ID No. 5)

inverse: 5'-CCA TCC GAG TAC GTG C-3'   (SEQ ID No. 6)

Cercospora nicotianae tubulin:
direct:  5'-ATC GAT AAC GAG GCC C-3'   (SEQ ID No. 7)

inverse: 5'-ACA TCG TAA GTC CTC GG-3'  (SEQ ID No. 8)
```

All the plants contain the plasmid pPAF115 according to the invention.

3.2.—Quantitative RT-PCR

The RNA of the events obtained is extracted and a reverse transcription is carried out before performing a quantitative PCR. The reverse transcription is carried out from 4 μg of RNA using random primers. The quantitative PCR is carried out according to this scheme:

| | |
| --- | --- |
| cDNA 100 ng tobacco tubulin | cDNA 100 ng *Cercospora* tubulin |
| cDNA 10 ng tobacco tubulin | cDNA 10 ng *Cercospora* tubulin |
| RNA 100 ng tobacco tubulin | RNA 100 ng *Cercospora* tubulin |
| RNA 10 ng tobacco tubulin | RNA 10 ng *Cercospora* tubulin |

The RNA is used to carry out the PCR reaction in order to ensure that the detection of DNA obtained with the cDNA is indeed due to an amplification of complementary DNA and not of contaminating genomic DNA (the amplification from the RNA must be zero).

The detection of the tobacco tubulin complementary DNA by virtue of the use of the primers mentioned below (SEQ ID No. 9 and SEQ ID No. 10) serves as a reference expression level. The level of expression of the transgene was calculated relative to this expression of tobacco tubulin.

```
Tobacco tubulin
direct
5'-GAA AAC ACG TCC CTC G-3'    (SEQ ID No. 9)

inverse
5'-TCT TGC CGT AGT CCA C-3'    (SEQ ID No. 10)
```

For all the experiments:

The RNA controls are negative, there is therefore no contamination with genomic DNA.

The difference in expression between the concentrations of 100 and 10 ng is constant and in accordance with expectations for 10-fold dilutions.

FIG. 3 shows the position of the *Cercospora nicotianae* tubulin primers on the DNA and RNA sequences comprising the sense-intron-antisense assembly as defined by the sequence identifier SEQ ID No. 4. The dashed lines represent diagrammatically the primers with which the quantitative PCR (qPCR) is carried out after the reverse transcription (RT).

The qPCR can detect the transcripts derived from the construct according to the invention only if they are not degraded. The RT-qPCR detects only the long transcripts, mRNA or dsRNA.

| Event | Level of detection (quantitative RT-PCR) | Results |
|---|---|---|
| WT | --- | No PCR detection of the construct<br>No detection of RNA of the construct |
| 14, 15 | +/− | Positive but weak PCR detection of the construct<br>Weak detection of RNA of the construct |
| 19 | + | Positive PCR detection of the construct<br>Clear detection of RNA of the construct |

"+" signifies that the signal is clearly detected by RT-qPCR
"+/−" signifies that the signal is weakly detected
"---" corresponds to the absence of the transgene 3.3.—Quantitative RT-PCR in View of the In Vivo Tests The in vivo tests are carried out on the T0 plants described above. This involves the events: 14, 15, 19 and WT. For these 4 events, clones derived from the initial T0 plant will therefore be used to carry out the tests. These clones are produced by cutting out from the leaves of each event, cultured again in vitro and regenerated (see above). In order to carry out a rapid control, a quantitative RT-PCR analysis is carried out on one clone of the events 14, 19 and WT (14A, 19A and WT, respectively).

All the controls (RNA, WT, and internal reference (tobacco tubulin)) are correct. Following validation of the controls, a level of expression can be given for each clone: the results are expressed qualitatively as a function of the values obtained by virtue of the quantitative PCR.

| Event | Level of expression (quantitative RT-PCR) | Results |
|---|---|---|
| WT | --- | No PCR detection of the construct<br>No detection of RNA of the construct |
| 14A | +/− | Positive but weak PCR detection of the construct<br>Weak detection of RNA of the construct |
| 19A | + | Positive PCR detection of the construct<br>Clear detection of RNA of the construct |

"+" signifies that the signal is clearly detected by RT-qPCR
"+/−" signifies that the signal is weakly detected
"---" corresponds to the absence of the transgene 4.—Pathological Tests In Vivo for Evaluating the Resistance of the Transgenic Tobacco Plants to Infection with *Cercospora nicotianae*

Plant Material:

Clones (at least nine) derived from the T0 events at a developmental stage of the plants comprising at least 5 developed leaves.

Production: S2 glass (25° C. daytime/20° C. night time; 60% RH; photoperiod 15 H of light).

Inoculum:

Suspension of *Cercospora nicotianae* (approximately $10^4$ spores/ml)

Evaluation of Symptoms:

The intensity of the symptoms is determined according to biological criteria as a function of the size and of the appearance of the lesions observed on the leaves. Thus, as can be seen in FIG. 4, the mark 1 corresponds to the visualization of very slight, barely perceptible, marks on the leaf. The mark 2 corresponds to clear, but very few, marks on the leaf. The mark 3 corresponds to clear and numerous marks on the leaf. The mark 4 corresponds to very clear and very numerous marks with the presence of large marks. The mark 5 corresponds either to complete rotting of the leaf, or to numerous very large marks. The differences between 1, 2, 3, 4 and 5 therefore correspond to real and clear differences in symptoms. Thus, plants having symptom marks of 4 or 5 are considered to be very severely affected. Plants with a mark of 3 are affected but remain acceptable. Plants with a mark of 2 are weakly affected and those with a mark of 1 are only very weakly affected.

There are, moreover, three different readings:

1st reading: 10 days after inoculation

2nd reading: 21 days after inoculation

3rd reading: 1 month after inoculation

Furthermore, the determination of the percentage contamination of the foliar surface ranges from 0% to 100%. 0% corresponds to an observation where no symptom is visible on the leaf, there appears to be a complete absence of the pathogen. 100% corresponds to a leaf completely covered by the pathogen, i.e. a brown and rotten leaf. Since the result of the reading was obtained with the average of the leaves of the same plant, values that are so extreme cannot be obtained. It can thus be considered that, above 30% of foliar surface which is contaminated, the plant is very severely affected by the disease. Below 20%, the contamination can be judged to be weak and below 10-15% as very weak.

The results are presented in the form of histograms corresponding to the means of the plants per event (results at 28 days after infection). The confidence interval is represented for each histogram.

For each event, the number of plants analyzed is indicated below along with the corresponding number of leaves:

WT: 19 plants (87 leaves)
event 14: 14 plants (67 leaves)
event 15: 21 plants (102 leaves)
event 19: 12 plants (60 leaves).

The results of the in vivo test are clearly correlated with the molecular analyses: the detection of the long transcripts derived from the construct according to the invention is completely correlated with a weaker intensity of the symptoms and therefore resistance of the transgenic plant.

| | | | Pathological tests on T0 tobacco plants Results at 28 days after infection | |
|---|---|---|---|---|
| Event | Presence of the transgene | RT-qPCR Detection of long RNAs | % of contaminated foliar surface (confidence interval) | Intensity of symptoms (confidence interval) |
| WT | No | −−− | 37% (6.6) | 4 (0.26) |
| 14 | Yes | −/+ | 11% (3.8) | 2 (0.37) |
| 15 | Yes | −/+ | 17% (3.85) | 3 (0.22) |
| 19 | Yes | + | 19% (4.8) | 3.2 (0.34) |

−/+: weak detection
+: clear detection
−−−: no detection

The results presented below are established using statistically validated tests for biological assays. The population of each event makes it possible to establish statistically robust confidence intervals.

Example 2

Creation of a Rice Resistant to *Magnaporthe grisea*

*Magnaporthe grisea* is a pathogen of rice (*Oryza sativa*). The chosen target in *Magnaporthe grisea* is the buf gene.

The buf gene is a gene essential to the pathogenicity of *Magnaporthe grisea*. In the case of deletion, *Magnaporthe grisea* is non-virulent and cannot contaminate rice (Kawamura et al., 1997, Mol. Plant Microb. Interact., 10(4): 446-53).

1.—Construct Used to Transform Rice Cells

The construct used to transform rice is the plasmid called pPAF 74; it comprises the following selectable marker: a gene for resistance to gentamycin under the control of a bacterial promoter. The CaMV 35S promoter allows transcription of the DNA sequence comprising part of the sense sequence of the buf gene, represented by the sequence identifier SEQ ID No. 11, itself followed by the antisense sequence of this same buf gene which is partially deleted compared with the sense sequence, represented by the sequence identifier SEQ ID No. 12. A Nos terminator is downstream of the sense-antisense assembly which is represented by the sequence identifier SEQ ID No. 13. The *Oryza sativa* variety Nippon Bare is transformed with this vector pPAF 74.

2.—Transformation of Rice Tissues with the Solution of *Agrobacterium* Transformed with the Plasmid pPAF 74

The embryos are removed from the pericarp and are immersed in a solution of 70% ethanol for 1 min. They are then placed in one third-diluted commercial bleach for 30 min and stirred from time to time. Finally, they are rinsed 3 times with sterile water.

The embryos thus decontaminated are placed on the side (12 per dish), on NB medium (macroelements N6, FeEDTA, microelements B5, vitamins B5, myoinositol, proline glutamine, casein hydrolysate, sucrose, 2,4-D, phytagel). The dish is left half-open under the hood so as to dry the seed well (incubator at 28° C.—in the dark—17 to 20 days). After a period of 17 to 20 days (28° C.—in the dark), the small embryogenic units (nodules of diameter from 0.5 to 1 mm) which form from the primary callus, in contact with the medium, are excised and subcultured on NB medium in a 100×15 dish (incubator at 280° C.—in the dark—10 days).

A culture of *Agrobacteria* ($3\text{-}5\times10^9$ bacteria/ml ($OD_{600}$=1)) is used for the transformation.

An inoculation and a coculture must then be performed: Calluses of 3 to 5 mm, that are nicely round, rough, whitish and opaque, are immersed in the solution of agrobacteria containing the plasmid pPAF 74 ($3\text{-}5\times10^9$ bacteria/ml) (20 ml per dish) for 15 min with slight stirring.

The calluses are transferred onto sterile Whatman paper and are dried. The calluses are then placed in culture on R2-CS medium (macroelements R2-I, macroelements R2-II, FeEDTA, microelements R2, vitamins R2, glucose, 2,4-D, type I agarose) in the dark, at a temperature of 25° C., for 3 days (10 calluses per dish).

The calluses are transferred onto R2S selection medium (macroelements R2-I, macroelements R2-II, FeEDTA, microelements R2, vitamins R2, sucrose, 2,4-D, type I agarose, vancomycin, cefotaxime, hygromycin) (28° C.—in the dark—2 weeks). The calluses are subcultured on NBS medium (macroelements N6, FeEDTA, microelements B5, vitamins B5, myoinositol, proline, glutamine, casein hydrolysate, sucrose, 2,4-D, type I agarose, cefotaxime, vancomycin, hygromycin) (280° C.—in the dark—1 week). The proliferations (globules) are spread out around their callus of origin, so as to bring them into contact with the selection medium (280° C.—in the dark—1 to 2 weeks).

The Transformants Must then Enter into Maturation:

The resistant proliferations are subcultured (well-developed globules, yellow-white in color) on PR-AG medium (macroelements N6, FeEDTA, microelements B5, vitamins B5, myoinositol, proline, glutamine, casein hydrolysate, sucrose, ABA, BAP, ANA, type I agarose, cefotaxime, hygromycin, vancomycin), identifying the callus of origin (10 calluses per dish) (280° C.—in the dark—8 days).

Regeneration of the Transformants:

The calluses are subcultured on RN regeneration medium (macroelements N6, FeEDTA, microelements B5, vitamins B5, myoinositol, proline, glutamine, casein hydrolysate, sucrose, BAP, ANA, phytagel) (28° C.—continuous light—3 weeks).

The regenerated plants are subcultured in a tube (MS medium, sucrose, phytagel).

They are subsequently subcultured in compost, acclimatized, and cultivated under glass.

Acclimatation of the Transformed Plants:

The plantlets are acclimatized when they have become well developed in the tube (after approximately 3-4 weeks). The plantlet is removed from the tube. The roots are passed under a trickle of water in order to remove the agar. The end of the leaves and of the roots is cut. The dead leaves are removed. The plantlet is placed in a pot, in a small glasshouse ("small greenhouse") containing 1-2 cm of water or none at all in order to avoid rotting, with the door closed. The top of the small glasshouse is protected with absorbent paper. The assembly is placed in an in vitro culture chamber. The door is gradually half opened and the paper is removed. When the roots emerge from the pot (after approximately 15 days), the plants are planted out in compost, in a pot. Eight different events were obtained.

3.—Molecular Analyses Carried Out on the Transgenic Rice 3.1.—PCR

First PCR experiments are carried out on the genomic DNA of the various events in order to determine whether the latter contain the construct according to the invention. Primers for detecting the *Magnaporthe buf* gene were used.

| | Event | | | |
|---|---|---|---|---|
| | M | L | F | WT |
| buf | + | + | + | − |

WT: wild-type, nontransformed plant.

The sequences of primers used are as follows:

```
Magnaporthe buf:
Direct:
5'-TGA CCG TGT CTT TAC CA-3'    (SEQ ID No. 16)

Indirect:
5'-AGC AAC CAC ATT AAC AGT-3'   (SEQ ID No. 17)
```

All the plants contain the plasmid according to the invention.

3.2. Quantitative RT-PCR:

The RNA of these 4 events is extracted and a reverse transcription is carried out before performing a quantitative PCR. The reverse transcription is carried out from 4 μg of RNA using random primers. The quantitative PCR is carried out according to this scheme:

| | |
|---|---|
| cDNA 100 ng rice tubulin | cDNA 100 ng *Magnaporthe* buf |
| cDNA 10 ng rice tubulin | cDNA 10 ng *Magnaporthe* buf |
| RNA 100 ng rice tubulin | RNA 100 ng *Magnaporthe* buf |
| RNA 10 ng rice tubulin | RNA 10 ng *Magnaporthe* buf |

The RNA is used to carry out the PCR reaction in order to ensure that the detection of DNA obtained with the DNA is indeed due to an amplification of complementary DNA and not of contaminating genomic DNA (the amplification from the RNA must be zero).

The detection of tobacco tubulin complementary DNA serves as a reference expression level. The level of expression of the transgene was calculated relative to this expression of tobacco tubulin.

The sequences of primers are as follows:

```
Rice tubulin:
Direct:
5'-CAT TGA CTT CAC GCG G-3'     (SEQ ID No. 14)

Indirect:
5'-GAC ACT GGA TTT GAC GTT-3'   (SEQ ID No. 15)
```

-continued

```
Magnaporthe buf:
Direct:
5'-TGA CCG TGT CTT TAC CA-3'    (SEQ ID No. 16)

Indirect:
5'-AGC AAC CAC ATT AAC AGT-3'.  (SEQ ID No. 17)
```

For all the Experiments:

The RNA controls are negative, there is therefore no contamination with genomic DNA.

The difference in expression between the concentrations of 100 and 10 ng is constant and in accordance with expectations for 10-fold dilutions.

| Event | Expression level (quantitative RT-PCR) | Results |
|---|---|---|
| WT | −−− | No PCR detection of the construct<br>No detection of RNA corresponding to the buf gene |
| M | +/− | PCR detection of the construct<br>Weak detection of RNA corresponding to the buf construct |
| L | + | PCR detection of the construct<br>Clear detection of RNA corresponding to the buf construct |
| F | ++ | PCR detection of the construct<br>Very clear detection of RNA corresponding to the buf construct |

"+" signifies that the signal is detected by RT-qPCR
"−−−" corresponds to the absence of the transgene
"++" signifies that the signal is strongly detected by RT-qPCR.

4.—Pathological Tests In Vivo for Evaluating the Resistance of the Transgenic Rice Plants to Infection with *Magnaporthe grisea*

Plant Material:

T0 events at a developmental stage of the plants comprising at least 5 developed leaves.

Production: S2 glass

Inoculum:

Suspension of *Magnaporthe grisea* ($10^4$ spores/ml).

Evaluation of Symptoms:

The intensity of the symptoms is determined according to biological criteria as a function of the size and the appearance of the lesions observed on the leaves. Thus, the mark 1 corresponds to the visualization of very slight, barely perceptible, marks on the leaf. The mark 2 corresponds to clear, but very few, marks on the leaf. The mark 3 corresponds to clear and numerous marks on the leaf. The mark 4 corresponds to very clear and very numerous marks with the presence of large marks. The mark 5 corresponds either to complete rotting of the leaf, or to numerous very large marks. The mark 6 corresponds to a plant 100% affected by the disease.

The differences between 1, 2, 3, 4, 5 and 6 therefore correspond to real and clear differences in symptoms. Thus, plants having symptom marks of 6 are dead, the plants 4 or 5 are considered to be very severely affected. Plants with a mark of 3 are affected but remain acceptable. Plants with a mark of 2 are weakly affected and those with a mark of 1 are only very weakly affected.

Figure 1:
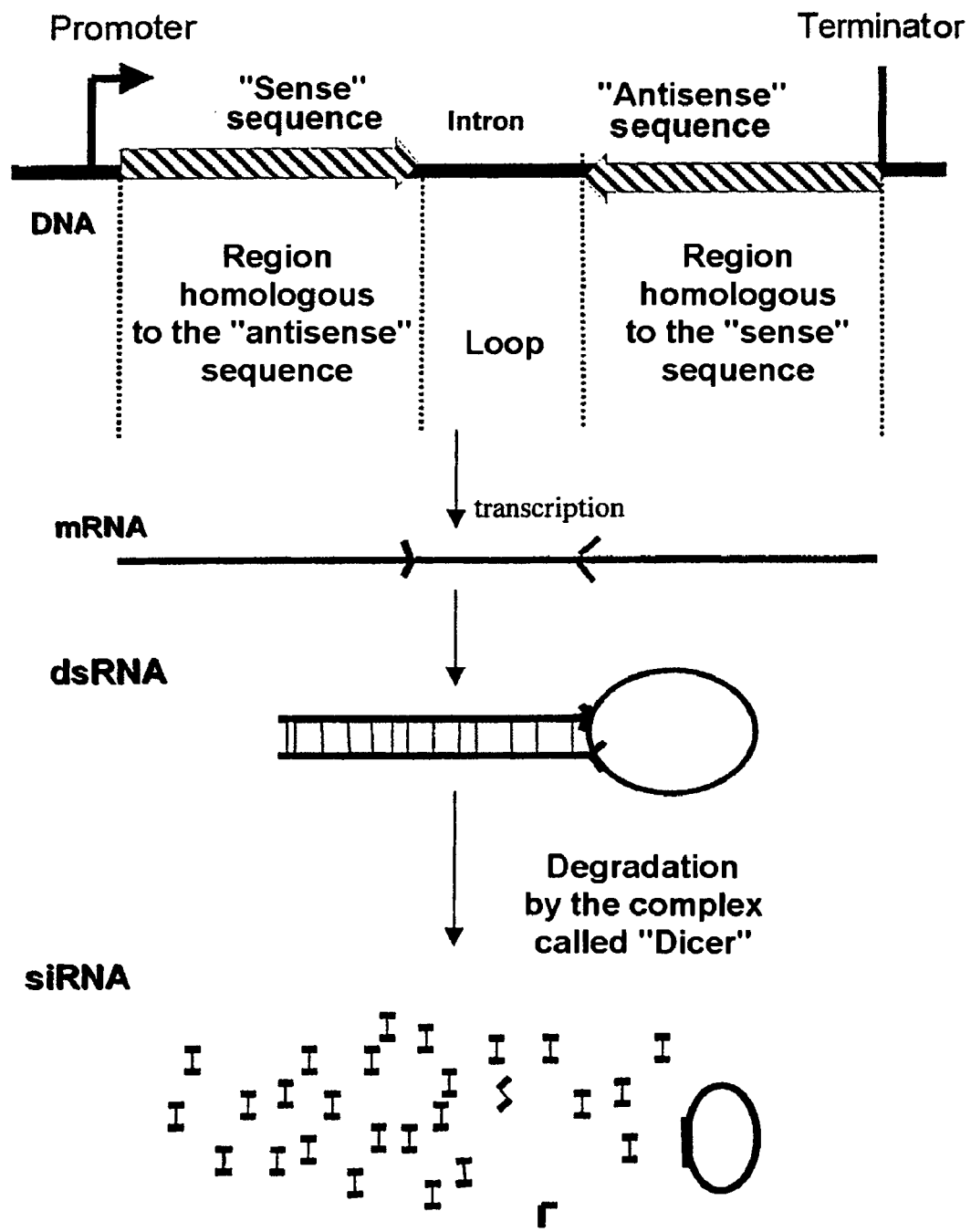
Figure 2:
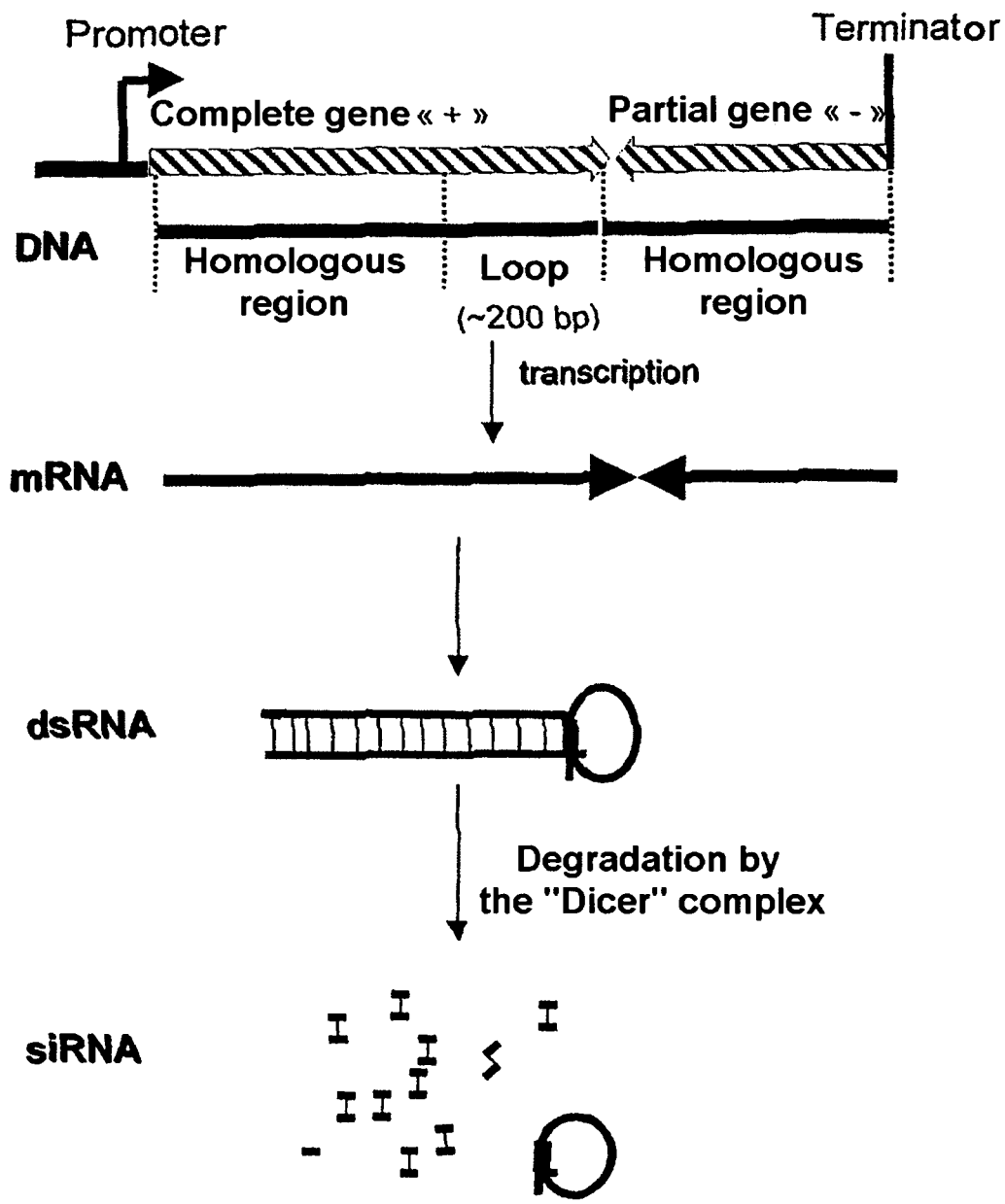
Figure 3:
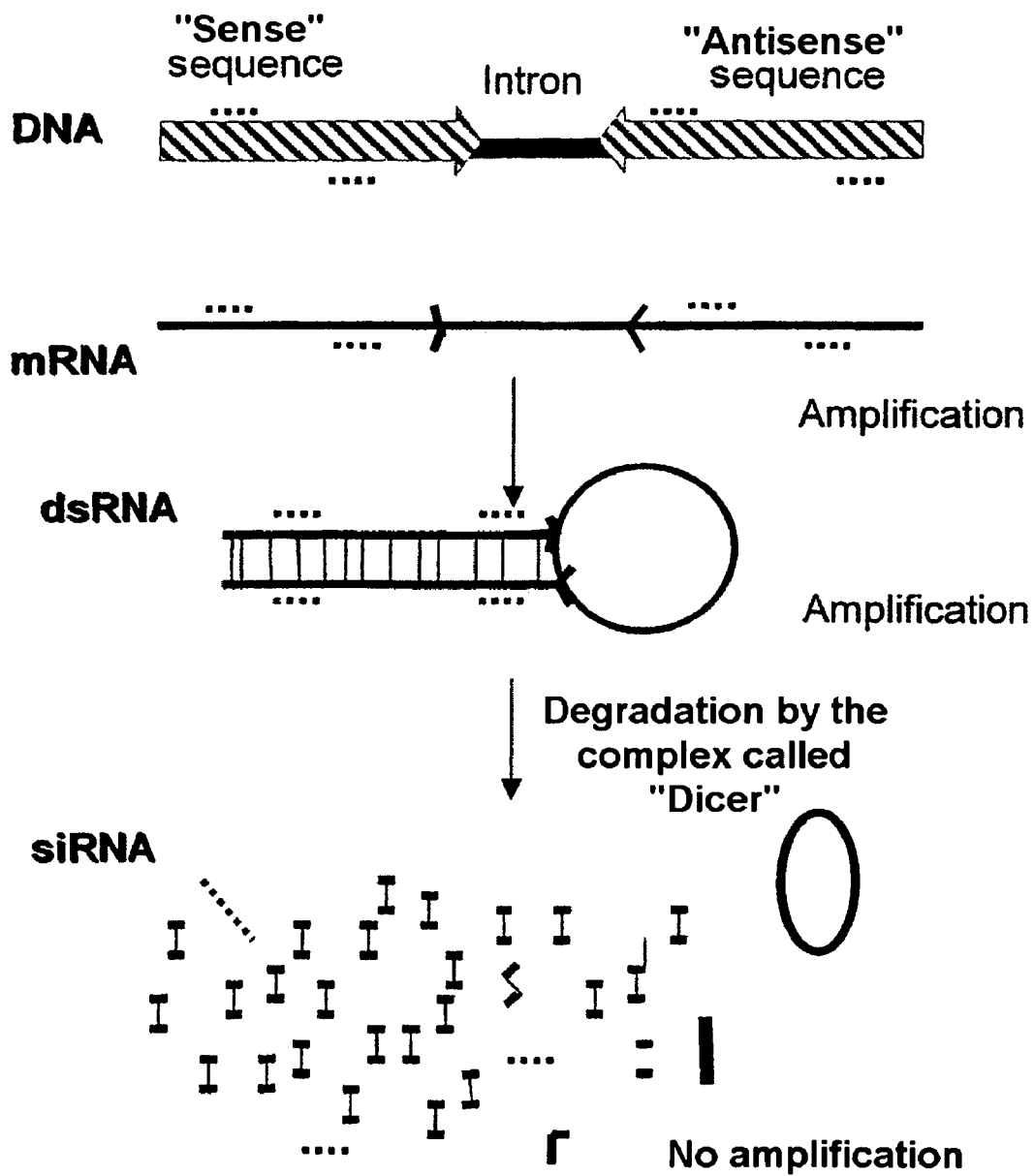
Figure 4:
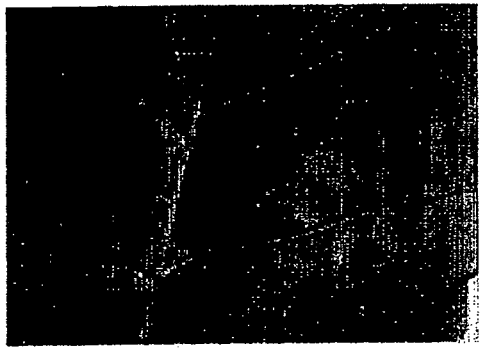
Figure 4:
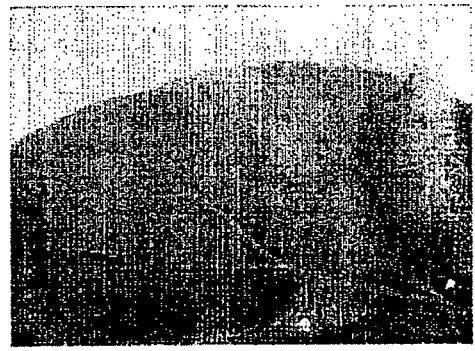
Figure 4:
Figure 4:
Figure 4:
Figure 4:
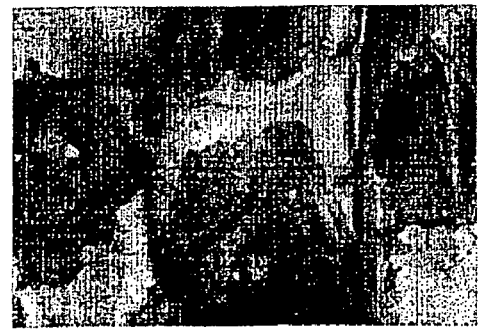
Figure 5:
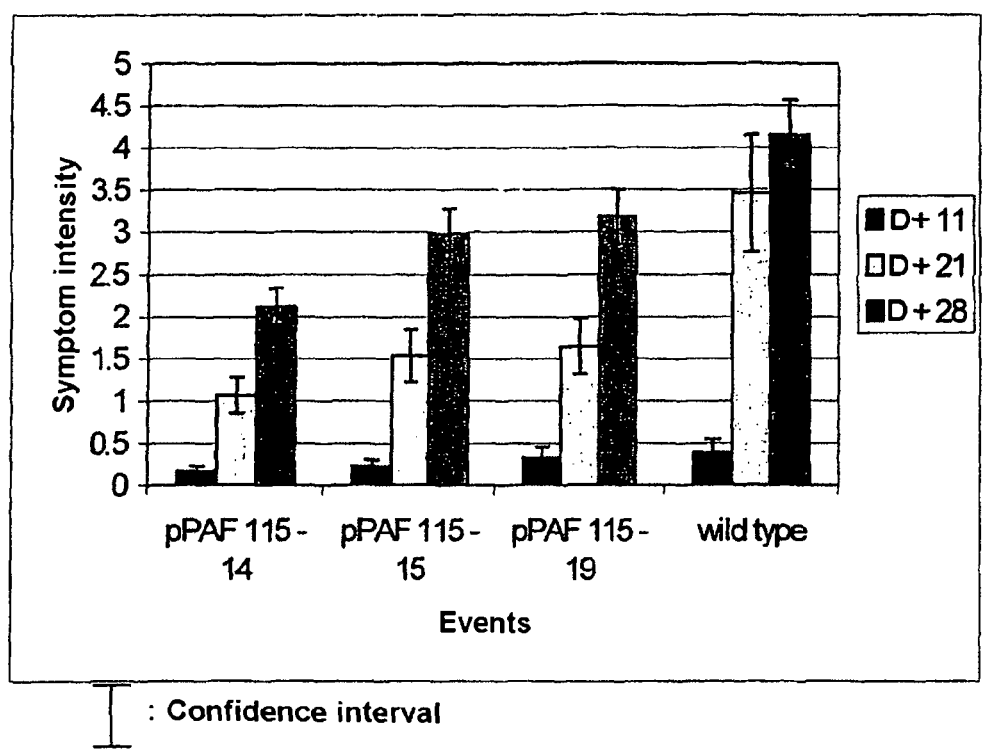
FIG. 5 represents the intensity of the symptoms noted for each event.
Figure 6:
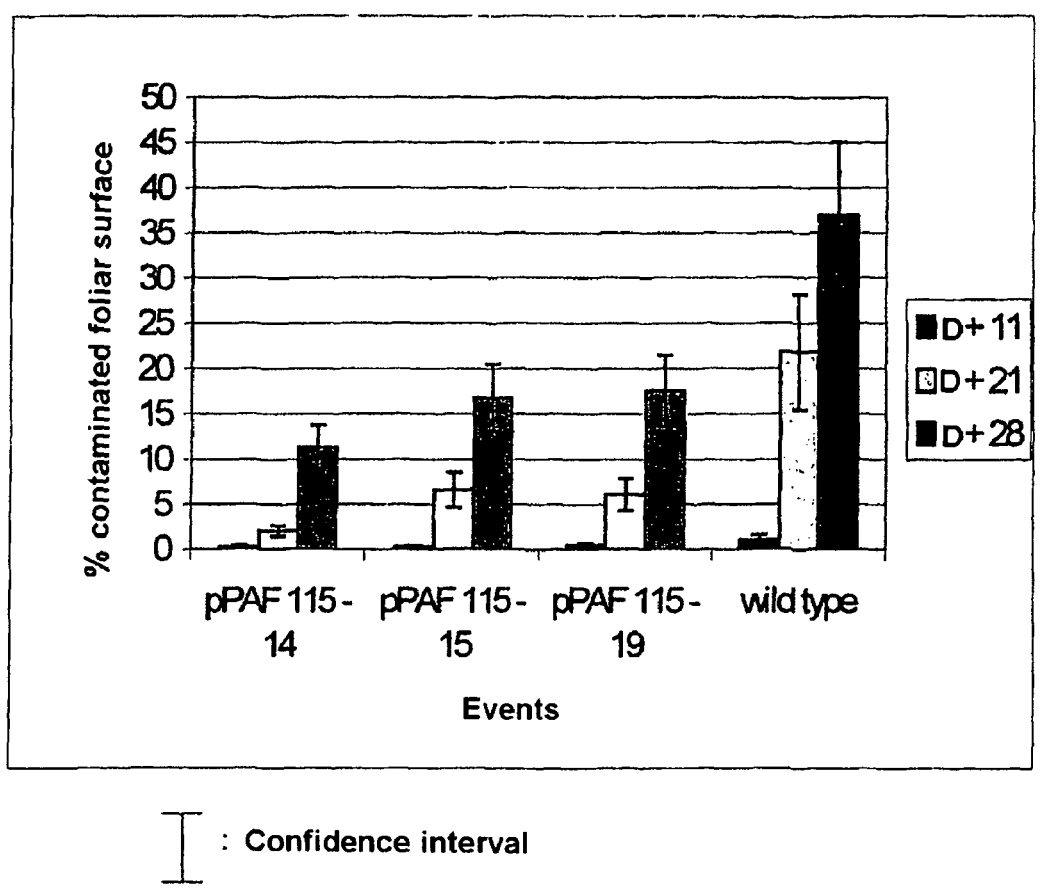
FIG. 6 represents the percentage of contaminated foliar surface for each event.
Figure 7:
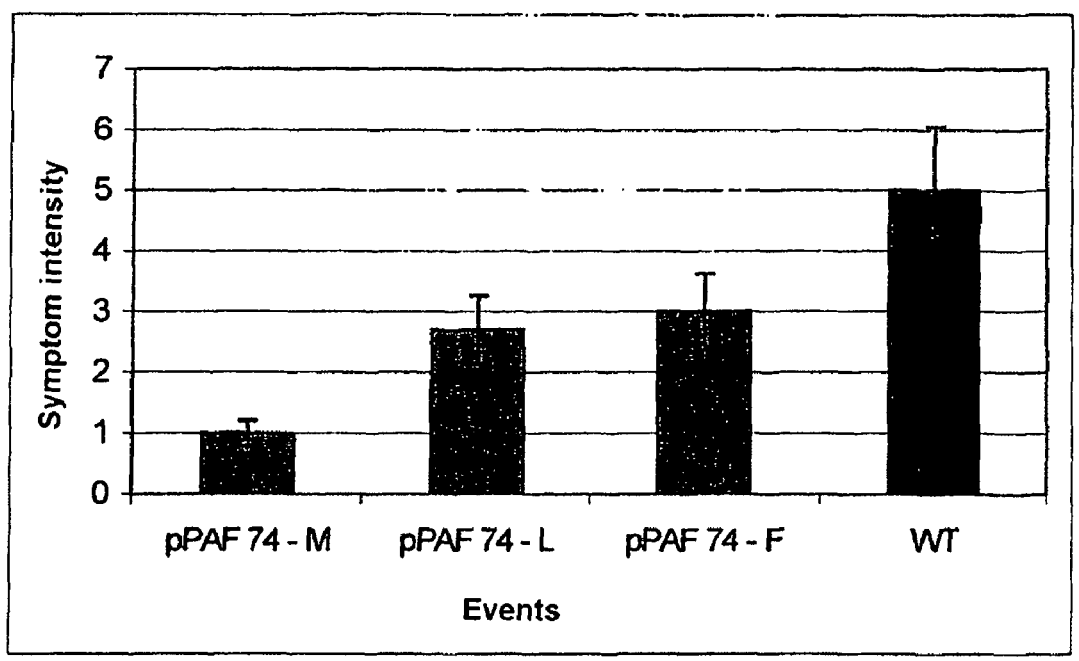
Figure 7:

The results are presented in the form of histograms corresponding to the means of the plants per event. The confidence interval is represented for each histogram. FIG. 7 presents the intensity of the symptoms noted for each event.

The results of the in vivo test are clearly correlated with the molecular analyses: the detection of the long transcripts derived from our construct is completely correlated with a weaker intensity of the symptoms and therefore resistance of the transgenic plant.

| Event | Presence of the transgene | RT-qPCR: detection of the long RNAs | Intensity of the symptoms 15 days after infection |
|---|---|---|---|
| WT | No | --- | 5-6 |
| M | Yes | −/+ | 1 |
| L | Yes | + | 2-3 |
| F | Yes | ++ | 2-3 |

−/+: weak detection
+: detection
++: strong detection
---: no detection

TABLE 1

| | |
|---|---|
| DQ026402 | *Mycosphaerella arachidis* strain 255 beta-tubulin gene, partial cds |
| DQ026347 | *Mycosphaerella coffeicola* strain 172 beta-tubulin gene, exon 8 and partial cds |
| DQ026336 | *Cercospora beticola* strain 21 beta-tubulin gene, exon 8 and partial cds |
| AY856374 | *Cercospora beticola* isolate AD-762 beta-tubulin (TUB1) gene, complete cds |
| AY856373 | *Cercospora beticola* isolate C-3 beta-tubulin (TUB1) gene, complete cds |
| AY373578 | *Cercospora kikuchii* isolate DLS5012-1A beta-tubulin gene, partial cds |
| AY373577 | *Cercospora kikuchii* isolate DLL6013-1B beta-tubulin gene, partial cds |
| AF146117 | *Cercospora piaropi* strain 2619 beta-tubulin (tub) gene, partial cds |
| AF146116 | *Cercospora beticola* strain Cb beta-tubulin (tub) gene, partial cds |
| AF146115 | *Cercospora piaropi* strain TX20 beta-tubulin (tub) gene, partial cds |
| AF146114 | *Cercospora piaropi* strain TX15 beta-tubulin (tub) gene, partial cds |
| AF146113 | *Cercospora piaropi* strain TX18 beta-tubulin (tub) gene, partial cds |
| AF146112 | *Cercospora piaropi* strain 62-4 beta-tubulin (tub) gene, partial cds |
| AF146111 | *Cercospora piaropi* strain WHK beta-tubulin (tub) gene, partial cds |
| AF146110 | *Cercospora piaropi* strain I75-102 beta-tubulin-like (tub) gene, partial sequence |
| AF146109 | *Cercospora piaropi* strain 62-2 beta-tubulin (tub) gene, partial cds |
| AF146108 | *Cercospora piaropi* strain 400 beta-tubulin (tub) gene, partial cds |
| AF146107 | *Cercospora piaropi* strain 34 beta-tubulin (tub) gene, partial cds |
| AF146106 | *Cercospora piaropi* strain 18 beta-tubulin (tub) gene, partial cds |
| AF146105 | *Cercospora piaropi* strain 114 beta-tubulin (tub) gene, partial cds |
| AF146104 | *Cercospora piaropi* strain RR29 beta-tubulin (tub) gene, partial cds |
| AF146103 | *Cercospora piaropi* strain BA57 beta-tubulin (tub) gene, partial cds |
| AF146102 | *Cercospora piaropi* strain WHV beta-tubulin (tub) gene, partial cds |
| AF146101 | *Cercospora piaropi* strain WH9BR beta-tubulin (tub) gene, partial cds |
| AF146100 | *Cercospora piaropi* strain WH83 beta-tubulin (tub) gene, partial cds |
| AF146099 | *Cercospora piaropi* strain 2867 beta-tubulin (tub) gene, partial cds |
| AF146098 | *Cercospora piaropi* strain 28-1 beta-tubulin (tub) gene, partial cds |
| AF146097 | *Cercospora piaropi* strain 10 beta-tubulin (tub) gene, partial cds |
| AF146096 | *Cercospora piaropi* strain MX3 beta-tubulin (tub) gene, partial cds |
| XM_370153 | *Magnaporthe grisea* 70-15 chromosome II hypothetical protein (MG06650.4) partial mRNA |
| XM_368640 | *Magnaporthe grisea* 70-15 chromosome VI hypothetical protein (MG00604.4) partial mRNA |
| XM_368283 | *Magnaporthe grisea* 70-15 chromosome VI hypothetical protein (MG00961.4) partial mRNA |
| AY944078 | *Magnaporthe oryzae* isolate CH072 beta-tubulin 1 gene, partial cds |
| AY944077 | *Magnaporthe oryzae* isolate SJ10-2-1 beta-tubulin 1 gene, partial cds |
| AY944076 | *Magnaporthe oryzae* isolate SAG00T15 beta-tubulin 1 gene, partial cds |
| AY063737 | *Magnaporthe grisea* isolate 8470 beta-tubulin gene, partial cds |
| AY063736 | *Magnaporthe grisea* isolate 8465 beta-tubulin gene, partial cds |
| AF396004 | *Magnaporthe salvinii* beta-tubulin gene, partial cds |
| AF396000 | *Magnaporthe grisea* strain A119 beta-tubulin gene, partial cds |
| AF395999 | *Magnaporthe grisea* strain Py-D beta-tubulin gene, partial cds |
| AF395998 | *Magnaporthe grisea* strain 91T16 beta-tubulin gene, partial cds |
| AF395997 | *Magnaporthe grisea* strain 81T4 beta-tubulin gene, partial cds |
| AF395996 | *Magnaporthe grisea* strain JP34 beta-tubulin gene, partial cds |
| AF395995 | *Magnaporthe grisea* strain RW12 beta-tubulin gene, partial cds |
| AF395994 | *Magnaporthe grisea* strain NI909 beta-tubulin gene, partial cds |
| AF395993 | *Magnaporthe grisea* strain 1122 beta-tubulin gene, partial cds |
| AF395992 | *Magnaporthe grisea* strain 330 beta-tubulin gene, partial cds |
| AF395991 | *Magnaporthe grisea* strain 365 beta-tubulin gene, partial cds |
| AF395990 | *Magnaporthe grisea* strain T28 beta-tubulin gene, partial cds |
| AF395989 | *Magnaporthe grisea* strain BK-19 beta-tubulin gene, partial cds |
| AF395988 | *Magnaporthe grisea* strain BK-6 beta-tubulin gene, partial cds |
| AF395987 | *Magnaporthe grisea* strain ML-56 beta-tubulin gene, partial cds |

TABLE 1-continued

| | |
|---|---|
| AF395986 | *Magnaporthe grisea* strain R707-1E beta-tubulin gene, partial cds |
| AF395985 | *Magnaporthe grisea* strain R694-2b beta-tubulin gene, partial cds |
| AF395984 | *Magnaporthe grisea* strain Guy11 beta-tubulin gene, partial cds |
| AF395983 | *Magnaporthe grisea* strain A598 beta-tubulin gene, partial cds |
| AF395982 | *Magnaporthe grisea* strain C10 beta-tubulin gene, partial cds |
| AF395981 | *Magnaporthe grisea* strain A264 beta-tubulin gene, partial cds |
| AF395980 | *Magnaporthe grisea* strain ML-91 beta-tubulin gene, partial cds |
| AF395979 | *Magnaporthe grisea* strain G48 beta-tubulin gene, partial cds |
| AF395978 | *Magnaporthe grisea* strain A347 beta-tubulin gene, partial cds |
| AF395977 | *Magnaporthe grisea* strain K76-79 beta-tubulin gene, partial cds |
| AF395976 | *Magnaporthe grisea* strain 1152 beta-tubulin gene, partial cds |
| AY944090 | *Magnaporthe oryzae* isolate SJ-5-1-2 chitin synthase 1 gene, partial cds |
| AY944089 | *Magnaporthe oryzae* isolate G48 chitin synthase 1 gene, partial cds |
| AY944088 | *Magnaporthe oryzae* isolate ML91 chitin synthase 1 gene, partial eds |
| AY944087 | *Magnaporthe oryzae* isolate GUY11 chitin synthase 1 gene, partial cds |
| AY944086 | *Magnaporthe oryzae* isolate G8 chitin synthase 1 gene, partial cds |
| AY944085 | *Magnaporthe oryzae* isolate G17 chitin synthase 1 gene, partial cds |
| AY944084 | *Magnaporthe oryzae* isolate G119 chitin synthase 1 gene, partial cds |
| AY944083 | *Magnaporthe oryzae* isolate BK6 chitin synthase 1 gene, partial cds |
| AY944082 | *Magnaporthe oryzae* isolate A119 chitin synthase 1 gene, partial cds |
| AY944081 | *Magnaporthe oryzae* isolate 1122 chitin synthase 1 gene, partial cds |
| AY944080 | *Magnaporthe oryzae* isolate 365 chitin synthase 1 gene, partial cds |
| AB018251 | *Magnaporthe grisea* gene for Csm1, complete cds |
| X96416 | *M. grisea* CHS4 gene |
| X96415 | *M. grisea* CHS3 gene |
| X96414 | *M. grisea* CHS2 gene |
| X96413 | *M. grisea* CHS1 gene |
| AF020528 | *Magnaporthe grisea* Class IV chitin synthase (chs4) gene, complete cds |

TABLE 2

| Plant | Diseases |
|---|---|
| Barley (*Hordeum vulgare* L.) | Anthracnose<br>*Colletotrichum graminicola* (Ces.) G. W. Wils.<br>*Glomerella graminicola* Politis [teleomorph]<br>Barley stripe<br>*Drechslera graminea* (Rabenh.) Shoemaker<br>*Cephalosporium* stripe<br>*Hymenula cerealis* Ellis & Everh. = *Cephalosporium gramineum* Nisikado & Ikata in Nisikado el al.<br>Common root rot, crown rot and seedling blight<br>*Bipolaris sorokiniana* (Sacc.) Shoemaker<br>*Fusarium culmorum* (Wm. G. Smith) Sacc.<br>*F. graminearum* Schwabe<br>*Gibberella zeae* (Schwein.) Petch [teleomorph]<br>Downy mildew<br>*Sclerophthora rayssiae* Kenneth et al.<br>Dwarf bunt<br>*Tilletia controversa* Kuhn in Rebenh.<br>Ergot<br>*Claviceps purpurea* (Fr.:Fr.) Tul.<br>*Sphacelia segetum* Lev. [anamorph]<br>Eyespot<br>*Pseudocercosoporella herpotrichoides* (Fron) Deighton<br>*Tapesia yallundae* Wallwork & Spooner [teleomorph]<br>Halo spot<br>*Pseudoseptoria donacis* (Pass.) Sutton = *Selenophoma donacis* (Pass.) R. Sprague & A. G. Johnson = *Septoria donacis*<br>Kernel blight = black point<br>*Alternaria* spp.<br>*Arthrinium arundinis* Dyko. & Sutton<br>*Apiospora montagnei* Sacc. [teleomorph]<br>*Cochliobolus sativus* (Ito & Kuribayashi) Drechs. Ex Dastur<br>*Fusarium* spp.<br>Leaf spot<br>*Ascochyta hordei* K. Hara (United States, Japan)<br>*A. graminea* (Sacc.) R. Sprague & A. G. Johnson<br>*A. sorghi* Sacc.<br>*A. tritici* S. Hori & Enjoji<br>Net blotch<br>*Drechslera teres* (Sacc.) Shoemaker<br>*Pyrenophora teres* Drechs. [teleomorph]<br>Net blotch (spot form)<br>*Drechslera teres* f. *maculata* Smedeg. |

TABLE 2-continued

| Plant | Diseases |
|---|---|
| | Powdery mildew |
| | *Erysiphe graminis* DC. f. sp. *hordei* Em. Marchal = *Blumeria graminis* (DC.) E. O. Speer |
| | *Oidium monilioides* (Nees) Link [anamorph] |
| | *Pythium* root rot |
| | *Pythium* spp. |
| | *P. arrhenomanes* Drechs. |
| | *P. graminicola* Subramanian |
| | *P. tardicrescens* Vanderpool |
| | *Rhizoctonia* root rot |
| | *Rhizoctonia solani* Kuhn |
| | *Thanatephorus cucumeris* (A. B. Frank) Donk [teleomorph] |
| | Rusts |
| | Crown rust |
| | *Puccinia coronata* Corda |
| | Leaf rust |
| | *Puccinia hordei* Otth |
| | Stem rust |
| | *Puccinia graminis* Pers.:Pers. |
| | Stripe rust = yellow rust |
| | *Puccinia striiformis* Westend. |
| | Scab = head blight |
| | *Fusarium* spp. |
| | *F. graminearum* Schwabe |
| | Scald |
| | *Rhynchosporium secalis* (Oudem.) J. J. Davis |
| | *Septoria* speckled leaf blotch |
| | *Septoria passerinni* Sacc. |
| | *Stagonospora avenae* f. sp. *triticea* T. Johnson |
| | Sharp eyespot |
| | *Rhizoctonia cerealis* Van der Hoeven |
| | *Ceratobasidium cereale* D. Murray & L. L. Burpee [teleomorph] |
| | Smuts |
| | Covered smut |
| | *Ustilago hordei* (Pers.) Lagerh. |
| | False loose smut |
| | *Ustilago avenae* (Pers.) Rostr. = *U. nigra* Tapke |
| | Loose smut |
| | *Ustilago tritici* (Pers.) Rostr. = *U. nuda* (C. N. Jensen) Rostr., nom. nud. |
| | Snow molds |
| | Gray snow mold = *Typhula* blight |
| | *Typhula incarnata* Fr. |
| | *T. ishikariensis* Imai |
| | Pink snow mold = *Fusarium* patch |
| | *Microdochium nivale* (Fr.) Samuel & I. C. Hallett = *Fusarium nivale* (Fr.) Sorauer |
| | *Monographella nivalis* (Schaffnit) E. Müller [teleomorph] |
| | Speckled snow mold |
| | *Typhula idahoensis* Remsberg |
| | Snow rot |
| | *Pythium iwayamai* Ito |
| | *P. okanoganense* Lipps |
| | *P. paddicum* Harane |
| | Snow scald = *Sclerotinia* snow mold |
| | *Myriosclerotinia borealis* (Bubak & Vleugel) L. M. Kohn = *Sclerotinia borealis* Bubak & Vleugel |
| | Southern blight |
| | *Sclerotium rolfsii* Sacc. (India, California, Puerto Rico) |
| | *Athelia rolfsii* (Curzi) Tu & Kimbrough [teleomorph] |
| | Spot blotch |
| | *Cochliobolus sativus* (Ito & Kuribayashi) Drechs. ex Dastur |
| | *Drechslera teres* (Sacc.) Shoemaker [anamorph] |
| | *Stagonospora* blotch |
| | *Stagonospora avenae* f. sp. *triticea* T. Johnson |
| | *Phaeosphaeria avenaria* f. sp. *triticea* T. Johnson [teleomorph] |
| | *Stagonospora nodrum* (Berk.) Castellani & E. G. Germano = *Septoria nodorum* (Berk.) Berk. in Berk. & Broome |
| | *Phaeosphaeria nodorum* (E. Muller) Hedjaroude [teleomorph] |
| | Take-all |

TABLE 2-continued

| Plant | Diseases |
|---|---|
| | *Gaeumannomyces graminis* var. *tritici* J. Walker |
| | Tan spot |
| | *Pyrenophora tritici-repentis* (Died.) Drechs. = *P. trichostoma* |
| | (Fr.) Fuckel |
| | *Drechslera tritici-repentis* (Died.) Shoemaker [anamorph] = *Helminthosporium* |
| | *tritici-repentis* Died. |
| | *Verticillium* wilt |
| | *Verticillium dahliae* Kleb. (Idaho) |
| | *Wirrega* blotch |
| | *Drechslera wirreganensis* Wallwork et al. (Australia) |
| Beet | *Alternaria* leaf spot |
| (*Beta vulgaris* L.) | *Alternaria alternata* (Fr.:Fr.) Keissl. |
| | *A. brassicae* (Berk.) Sacc. |
| | Anthracnose* |
| | *Colletotrichum dematium* (Pers.) Grove f. *spinaciae* |
| | (Ellis & Halst.) Arx |
| | *Aphanomyces* root rot (black root) |
| | *Aphanomyces cochlioides* Drechs. |
| | Black wood vessel* |
| | *Pythium irregulare* Buisman |
| | *Cercospora* leaf spot |
| | *Cercospora beticola* Sacc. |
| | Charcoal rot |
| | *Macrophomina phaseolina* (Tassi) Goidanich |
| | *Choanephora* rot* |
| | *Choanephora cucurbitatum* (Berk. & Ravenel) Thaxt. |
| | Damping-off, black leg, black root and seedling blight |
| | *Aphanomyces cochlioides* Drechs. |
| | *Cylindrocladium* sp.* |
| | *Fusarium* spp. |
| | *Phoma betae* A. B. Frank |
| | *Pleospora betae* (Berl.) Nevodovsky [teleomorph] |
| | *Pythium* spp. |
| | *Rhizoctonia solani* Kühn |
| | *Thanatephorus cucumeris* (A. B. Frank) Donk |
| | [teleomorph] |
| | Downy mildew |
| | *Peronospora farinosa* (Fr.:Fr.) Fr. = *P. farinosa* |
| | (Fr.:Fr) Fr. f. sp. *betae* Byford = *P. schachtii* |
| | Fuckel |
| | *Fusarium* yellows |
| | *Fusarium oxysporum* Schlechtend.:Fr. f. sp. *spinaciae* |
| | (Sherb.) W. C. Snyder & H. N. Hans. |
| | *Fusarium* yellows and root rot |
| | *Fusarium oxysporum* Schlechtend.:Fr. f. sp. *betae* (D. Stewart) |
| | W. C. Snyder & H. N. Hans. (Texas isolates) |
| | Leaf gall (beet tumor, or crown wart) |
| | *Physoderma leproides* (Trab.) Karling = *Urophlyctis* |
| | *leproides* (Trab.) Magnus |
| | *Phoma* leaf spot and root rot |
| | *Phoma betae* A. B. Frank |
| | *Phymatotrichum* root rot (cotton root rot) |
| | *Phymatotrichopsis omnivora* (Duggar) Hennebert = *Phymatotrichum* |
| | *omnivorum* Duggar |
| | *Phytophthora* wet rot |
| | Phytophthora drechsleri Tucker |
| | Powdery mildew |
| | *Erysiphe polygoni* DC. = *E. betae* |
| | Weltzien |
| | *Pythium* root rot |
| | *Pythium aphanidermatum* (Edson) Fitzp. |
| | *P. deliense* Meurs |
| | *Ramularia* leaf spot |
| | *Ramulariabeticola* Fautrey & Lambotte |
| | *Rhizoctonia* foliar blight, crown and root rot |
| | *Rhizoctonia solani* Kühn |
| | *Rhizopus* root rot |
| | *Rhizopus arrhizus* A. Fischer |
| | *R. stolonifer* (Ehrenb.:Fr.) Vuill. |
| | Rust |
| | *Uromycesbetae* J. Kickx fil. |
| | *Sclerotinia* crown & root rot |
| | *Sclerotinia sclerotiorum* (Lib.) de Bary |
| | Seedling rust |
| | *Puccinia subnitens* Dietel |
| | Slime molds* |
| | *Physarum cinereum* (Batsch) Pers. |

TABLE 2-continued

| Plant | Diseases |
|---|---|
| | Southern blight (*Sclerotium* root rot and stem rot)<br>*Sclerotium rolfsii* Sacc.<br>*Athelia rolfsii* (Curzi) Tu & Kimbrough [teleomorph]<br>Stemphylium leaf spot*<br>*Stemphylium botryosum* Wallr.<br>*Pleospora tarda* E. Simmons [teleomorph]<br>Storage rots<br>*Botrytis cinerea* Pers.: Fr.<br>*Botryotinia fuckeliana* (de Bary) Whetzel [teleomorph]<br>*Penicillium* spp.<br>*Phoma betae* A. B. Frank<br>Verticillium wilt<br>*Verticillium albo-atrum* Reinke & Berthier<br>Violet root rot<br>*Helicobasidium brebissonii* (Desmaz.) Donk<br>*Rhizoctonia crocorum* (Pers.:Fr.) DC. [anamorph] |
| Coffee<br>(*Coffea arabica* L. -<br>arabica<br>coffee)<br>(*Coffea<br>canephora* Pierre<br>ex Froehner -<br>robusta coffee) | Anthracnose<br>*Colletotrichum gloeosporioides* Penz<br>(teleomorph = *Glomerella cingulata* (Stonem.) Spauld, & Shrenk.)<br>*Colleotrichum kahawae* Waller & Bridge<br>Armillaria root rot<br>*Armillaria mellea* (Vahl ex Fries) Kummer<br>Bark disease<br>*Fusarium stilboides* Wollenw.<br>(teleomorph = *Gibberella stilboides*)<br>Berry blotch<br>*Cercospora coffeicola* Berk. & Cke<br>Black (*Rosellinia*) root rot<br>*Rosellinia* spp.<br>Black (seedling) root rot<br>*Rhizoctonia solani* Kuhn.<br>Blister spot<br>Virus (uncharacterised)<br>Brown blight<br>*Colleotrichum gloeosporioides* Penz.<br>(teleomorph = *Glomerella cingulata* (Stonem.) Spauld. & Schrenk<br>*Colletotrichum kahawae* Waller & Bridge<br>Brown eye spot<br>*Cercospora coffeicola* Berk. & Cke<br>Brown leaf spot<br>*Phoma costarricensis* Ech.<br>Canker<br>*Ceratocystis fimbriata* (Ell. & Halst.) Hunt<br>*Phomopsis coffeae* Bondarzeva-Monteverde<br>Collar rot<br>*Fusarium stilboides* Wollenz<br>(telemorph = *Gibberella stilboides*)<br>Coffee berry disease<br>*Colletotrichum kahawae* Waller & Bridge<br>Die-back<br>*Ascochta tarda* Stewart<br>Dry root rot<br>*Fusarium solani* (Mart.) Sacc.<br>Leaf blight<br>*Ascochyta tarda* Stewart<br>Leaf spot<br>*Phyllosticta coffeicola* Speg.<br>Pink disease<br>*Corticium salmonicola* Berk. & Br.<br>Red blister disease (robusta coffee)<br>*Cercospora coffeicola* Berk. & Br.<br>Red root rot<br>*Ganoderma philippi* (Bres & P. Henn.) Bres.<br>Root knot<br>*Meloidogyne* spp.<br>Rust (orange or leaf rust)<br>*Hemileia vastatrix* Berk. & Br.<br>Rust (powdery or grey rust)<br>*Hemileia coffeicola* Mauble. & Rog.<br>South America leaf spot<br>*Mycena citricola* (Berk. & Curt.) (=*Omphalia flavida* Maubl, & Rang. Anamorph = *Stilbum flavidum* Cke)<br>Thread blight<br>*Corticium koleroga* (Cke) Hoehnel |

TABLE 2-continued

| Plant | Diseases |
|---|---|
| | Tip blast<br>*Phoma* costarricensis Ech.<br>*Tracheomycosis* (Wilt)<br>*Gibberella xylarioides* Heim & Saccas<br>(anamorph = *Fusarium eylarioides* Steyaert)<br>Wilt<br>*Ceratocystis fimbriata* (Ell. & Halst.) Hunt<br>*Fusarium oxysporum* Schl. *f.* sp. *Coffea* (Garcia) Wellman<br>Warty berry<br>*Botrytis cinerea* Pers. Ex *Fries* var. *coffeae* Hendr. |
| Corn or Maize<br>(*Zea mays* L.) | Anthracnose leaf blight and anthracnose stalk rot<br>*Colletotrichum graminicola* (Ces.) G. W. Wils.<br>(teleomorph: *Glomerella graminicola* Politis)<br>*Glomerella tucumanensis* (Speg.) Arx & E. Muller<br>(anamorph: *Glomerella falcatum* Went)<br>*Aspergillus* ear and kernel rot<br>*Aspergillus flavus* Link:Fr.<br>Banded leaf and sheath spot*<br>*Rhizoctonia solani* Kühn = *Rhizoctonia microsclerotia* J. Matz<br>(teleomorph: *Thanatephorus cucumeris* (A. B. Frank) Donk)<br>Black bundle disease<br>*Acremonium strictum* W. Gams = *Cephalosporium acremonium* Auct. non Corda<br>Black kernel rot*<br>*Lasiodiplodia theobromae* (Pat.) Griffon & Maubl. = Botryodiplodia *theobromae* Pat.<br>Borde blanco*<br>*Marasmiellus* sp.<br>Brown spot (black spot, stalk rot)<br>*Physoderma maydis* (Miyabe) Miyabe<br>*Cephalosporium* kernel rot<br>*Acremonium strictum* W. Gams = *Cephalosporium acremonium* Auct. non Corda<br>Charcoal rot<br>*Macrophomina phaseolina* (Tassi) Goidanich<br>*Corticium* ear rot*<br>*Thanatephorus cucumeris* (A. B. Frank) Donk = *Corticium sasakii* (Shirai) Matsumoto<br>*Curvularia* leaf spot<br>*Curvularia clavata* P. C. Jain<br>*C. eragrostidis* (Henn.) J. A. Meyer = *C. maculans* (Bancroft) Boedijn<br>(teleomorph: *Cochliobolus eragrostidis* (Tsuda & Ueyama) Sivanesan<br>*Curvularia inaequalis* (Shear) Boedijn<br>*C. intermedia* Boedijn<br>(teleomorph: Cochliobolus intermedius R. R. Nelson)<br>*Curvularia lunata* (Wakk.) Boedijn<br>(teleomorph: *Cochliobolus lunatus* R. R. Nelson & Haasis)<br>*Curvularia pallescens* Boedijn<br>(teleomorph: *Cochliobolus pallescens* (Tsuda & Ueyama) Sivanesan)<br>*Curvularia senegalensis* (Speg.) Subramanian<br>*C. tuberculata* P. C. Jain<br>(teleomorph: *Cochliobolus tuberculatus* Sivanesan)<br>*Didymella* leaf spot*<br>*Didymella exitalis* (Morini) E. Muller<br>*Diplodia* ear rot and stalk rot<br>*Diplodia frumenti* Ellis & Everh.<br>(teleomorph: *Botryosphaeria festucae* (Lib.) Arx & E. Müller<br>*Diplodia* ear rot, stalk rot, seed rot and seedling blight<br>*Diplodia maydis* (Berk.) Sacc.<br>*Diplodia* leaf spot or leaf streak<br>*Stenocarpella macrospora* (Earle) Sutton = *Diplodia macrospora* Earle<br>Downy mildews:<br>Brown stripe downy mildew*<br>*Sclerophthora rayssiae* Kenneth et al. var. *zeae* Payak & Renfro<br>Crazy top downy mildew<br>*Sclerophthora macrospora* (Sacc.) Thirumalachar et al. = *Sclerospora macrospora* Sacc.<br>Green ear downy mildew (*graminicola* downy mildew)<br>*Sclerospora graminicola* (Sacc.) J. Schröt.<br>Java downy mildew*<br>*Peronosclerospora maydis* (Racib.) C. G. Shaw = *Sclerospora* |

TABLE 2-continued

| Plant | Diseases |
|---|---|
| | *maydis* (Racib.) Butler
Philippine downy mildew*
*Peronosclerospora philippinensis* (W. Weston) C. G. Shaw = *Sclerospora philippinensis* W. Weston
*Sorghum* downy mildew
*Peronosclerospora sorghi* (W. Weston & Uppal) C. G. Shaw = *Sclerospora sorghi* W. Weston & Uppal
Spontaneum downy mildew*
*Peronosclerospora spontanea* (W. Weston) C. G. Shaw = *Sclerospora spontanea* W. Weston
Sugarcane downy mildew*
*Peronosclerospora sacchari* (T. Miyake) Shirai & Hara = *Sclerospora sacchari* T. Miyake
Dry ear rot (cob, kernel and stalk rot)
*Nigrospora oryzae* (Berk. & Broome) Petch
(teleomorph: Khuskia oryzae H. J. Hudson)
Ear rots, minor
*Alternaria alternata* (Fr.:Fr.) Keissl. = *A. tenuis* Nees
*Aspergillus glaucus* Link:Fr.
*A. niger* Tiegh.
*Aspergillus* spp.
*Botrytis cinerea* Pers.:Fr.
(teleomorph: *Botryotinia fuckeliana* (de Bary) Whetzel)
*Cunninghamella* sp.
*Curvularia pallescens* Boedijn
*Doratomyces stemonitis* (Pers.:Fr.) F.J. = *Cephalotrichum stemonitis* (Pers.:Fr.) Link
*Fusarium culmorum* (Wm. G. Sm.) Sacc.
*Gonatobotrys simplex* Corda
*Pithomyces maydicus* (Sacc.) M. B. Ellis
*Rhizopus microsporus* Tiegh.
*R. stolonifer* (Ehrenb.:Fr.) Vuill. = *R. nigricans* Ehrenb.
*Scopulariopsis brumptii* Salvanet-Duval
Ergot* (horse's tooth, diente de caballo)
*Claviceps gigantea* Fuentes et al.
(anamorph: *Sphacelia* sp.)
Eyespot
*Aureobasidium zeae* (Narita & Hiratsuka) J. M. Dingley = *Kabatiella zeae* Narita & Hiratsuka
*Fusarium* ear and stalk rot
*Fusarium subglutinans* (Wollenweb. & Reinking) P. E. Nelson et al. = *F. moniliforme* J. Sheld. var. *subglutinans* Wollenweb. & Reinking
*Fusarium* kernel, root and stalk rot, seed rot and seedling blight
*Fusarium moniliforme* J. Sheld.
(teleomorph: *Gibberella fujikuroi* (Sawada) Ito in Ito & K. Kimura)
*Fusarium* stalk rot, seedling root rot
*Fusarium avenaceum* (Fr.:Fr.) Sacc.
(teleomorph: *Gibberella avenacea* R. J. Cooke)
*Gibberella* ear and stalk rot
*Gibberella zeae* (Schwein.) Petch
(anamorph: *Fusarium graminearum* Schwabe)
Gray ear rot
*Botryosphaeria zeae* (G. L. Stout) Arx & E. Müller = *Physalospora zeae* G. L. Stout
(anamorph: *Macrophoma zeae* Tehon & E. Y. Daniels)
Gray leaf spot (*Cercospora* leaf spot)
*Cercospora sorghi* Ellis & Everh. = *C. sorghi* Ellis & Everh. var. *maydis* Ellis & Everh.
*C. zeae-maydis* Tehon & E. Y. Daniels
*Helminthosporium* root rot
*Exserohilum pedicellatum* (A. W. Henry) K. J. Leonard & E. G. Suggs = *Helminthosporium pedicellatum* A. W. Henry
(teleomorph: *Setosphaeria pedicellata* (R. R. Nelson) K. J. Leonard & E. G. Suggs)
*Hormodendrum* ear rot (*Cladosporium* rot)
*Cladosporium cladosporioides* (Fresen.) G. A. De Vries = *Hormodendrum cladosporioides* (Fresen.) Sacc.
*C. herbarum* (Pers.:Fr.) Link
(teleomorph: *Mycosphaerella tassiana* (De Not.) Johans.)
*Hyalothyridium* leaf spot* |

TABLE 2-continued

| Plant | Diseases |
|---|---|

*Hyalothyridium maydis* Latterell & Rossi
Late wilt*
*Cephalosporium maydis* Samra et al.
Leaf spots, minor
*Alternaria alternata* (Fr.:Fr.) Keissl.
*Ascochyta maydis* G. L. Stout
*A. tritici* S. Hori & Enjoji
*A. zeicola* Ellis & Everh.
*Bipolaris victoriae* (F. Meehan & Murphy) Shoemaker = *Helminthosporium victoriae* F. Meehan & Murphy
(teleomorph: *Cochliobolus victoriae* R. R. Nelson)
*C. sativus* (Ito & Kuribayashi) Drechs. ex Dastur
(anamorph: *Bipolaris sorokiniana* (Sacc.) Shoemaker = *H. sorokinianum* Sacc. in Sorokin = *H. sativum* Pammel et al.)
*Epicoccum nigrum* Link
*Exserohilum prolatum* K. J. Leonard & E. G. Suggs = *Drechslera prolata* (K. J. Leonard & E. G. Suggs) Sivanesan
(teleomorph: *Setosphaeria prolata* K. J. Leonard & E. G. Suggs)
*Graphium penicillioides* Corda
*Leptosphaeria maydis* G. L. Stout
*Leptothyrium zeae* G. L. Stout
*Ophiosphaerella herpotricha* (Fr.:Fr.) J. C. Walker
(anamorph: *Scolecosporiella* sp.)
*Paraphaeosphaeria michotii* (Westend.) O. Eriksson
*Phoma* sp.
*Septoria zeae* G. L. Stout
*S. zeicola* G. L. Stout
*S. zeina* G. L. Stout
Northern corn leaf blight (white blast, crown stalk rot, stripe)
*Setosphaeria turcica* (Luttrell) K. J. Leonard & E. G. Suggs
(anamorph: Exserohilum turcicum (Pass.) K. J. Leonard & E. G. Suggs = *Helminthosporium turcicum* Pass.)
Northern corn leaf spot, *Helminthosporium* ear rot (race 1)
*Cochlioboluscarbonum* R. R. Nelson (anamorph: *Bipolaris zeicola* (G. L. Stout) Shoemaker = *Helminthosporium carbonum* Ullstrup)
*Penicillium* ear rot (blue eye, blue mold)
*Penicillium* spp.
*P. chrysogenum* Thom
*P. expansum* Link
*P. oxalicum* Currie & Thom
*Phaeocytostroma* stalk rot and root rot
*Phaeocytostroma ambiguum* (Mont.) Petr. & Syd. = *Phaeocytosporella zeae* G. L. Stout
*Phaeosphaeria* leaf spot*
*Phaeosphaeria maydis* (P. Henn.) Rane, Payak & Renfro = *Sphaerulina maydis* P. Henn.
*Physalospora* ear rot (*Botryosphaeria* ear rot)
*Botryosphaeria festucae* (Lib.) Arx & E. Müller = *Physalospora zeicola* Ellis & Everh.
(anamorph: *Diplodia frumenti* Ellis & Everh.)
Purple leaf sheath
Hemiparasitic bacteria and fungi
*Pyrenochaeta* stalk rot and root rot
*Phoma terrestris* E. M. Hans. = *Pyrenochaeta terrestris* (E. M. Hans.) Gorenz et al.
*Pythium* root rot
*Pythiumn* spp.
*P. arrhenomanes* Drechs.
*P. graminicola* Subramanian
*Pythium* stalk rot
*Pythium aphanidermatum* (Edson) Fitzp. = *P. butleri* L. Subramanian
Red kernel disease (ear mold, leaf and seed rot)
*Epicoccum nigrum* Link
*Rhizoctonia* ear rot (sclerotial rot)
*Rhizoctonia zeae* Voorhees
(teleomorph: *Waitea circinata* Warcup & Talbot)
*Rhizoctonia* root rot and stalk rot
*Rhizoctonia solani* Kühn
*R. zeae* Voorhees
Root rots, minor
*Alternaria alternata* (Fr.:Fr.) Keissl.
*Cercospora sorghi* Ellis & Everh.

TABLE 2-continued

| Plant | Diseases |
|---|---|
|  | *Dictochaeta fertilis* (S. J. Hughes & Kendrick) Holubova-Jechova<br>*Fusarium acuminatum* Ellis & Everh.<br>(teleomorph: *Gibberella acuminata* Wollenweb.)<br>*F. equiseti* (Corda) Sacc.<br>(teleomorph: *G. intricans* Wollenweb.)<br>*F. oxysporum* Schlechtend.:Fr.<br>*F. pallidoroseum* (Cooke) Sacc.<br>*F. poae* (Peck) Wollenweb.<br>*F. roseum* Link:Fr.<br>*G. cyanogena* (Desmaz.) Sacc.<br>(anamorph: *F. sulphureum* Schlechtend.)<br>*Microdochium bolleyi* (R. Sprague) DeHoog & Hermanides-Nijhof<br>*Mucor* sp.<br>*Periconia circinata* (L. Mangin) Sacc.<br>*Phytophthora cactorum* (Lebert & Cohn) J. Schrot.<br>*P. drechsleri* Tucker<br>*P. nicotianae* Breda de Haan var. *parasitica* (Dastur) G. M. Waterhouse<br>*Rhizopus arrhizus* A. Fischer<br>Rostratum leaf spot (*Helminthosporium* leaf disease, ear and stalk rot)<br>*Setosphaeria rostrata* K. J. Leonard (anamorph: *Exserohilum rostratum* (Drechs.) K. J. Leonard & E. G. Suggs = *Helminthosporium rostratum* Drechs.)<br>Rust, common corn<br>*Puccinia sorghi* Schwein.<br>Rust, southern corn<br>*Puccinia polysora* Underw.<br>Rust, tropical corn<br>*Physopella pallescens* (Arth.) Cummins & Ramachar<br>*P. zeae* (Mains) Cummins & Ramachar = *Angiopsora zeae* Mains<br>*Sclerotium* ear rot* (southern blight)<br>*Sclerotium rolfsii* Sacc.<br>(teleomorph: *Athelia rolfsii* (Curzi) Tu & Kimbrough)<br>Seed rot-seedling blight<br>*Bipolaris sorokiniana* (Sacc.) Shoemaker<br>*B. zeicola* (G. L. Stout) Shoemaker = *Helminthosporium carbonum* Ullstrup<br>*Diplodia maydis* (Berk.) Sacc.<br>*Exserohilum pedicillatum* (A. W. Henry) K. J. Leonard & E. G. Suggs<br>*Exserohilum turcicum* (Pass.) K. J. Leonard & E. G. Suggs = *Helminthosporium turcicum* Pass.<br>*Fusarium avenaceum* (Fr.:Fr.) Sacc.<br>*F. culmorum* (Wm. G. Sm.) Sacc.<br>*F. moniliforme* J. Sheld.<br>*Gibberella zeae* (Schwein.) Petch<br>(anamorph: *F. graminearum* Schwabe)<br>*Macrophomina phaseolina* (Tassi) Goidanich<br>*Penicillium* spp.<br>*Phomopsis* sp.<br>*Pythium* spp.<br>*Rhizoctonia solani* Kühn<br>*R. zeae* Voorhees<br>*Sclerotium rolfsii* Sacc.<br>*Spicaria* sp.<br>*Selenophoma* leaf spot*<br>*Selenophoma* sp.<br>Sheath rot<br>*Gaeumannomyces graminis* (Sacc.) Arx & D. Olivier<br>Shuck rot<br>*Myrothecium gramineum* Lib.<br>Silage mold<br>*Monascus purpureus* Went<br>*M. ruber* Tiegh.<br>Smut, common<br>*Ustilago zeae* (Beckm.) Unger = *U. maydis* (DC.) Corda<br>Smut, false<br>*Ustilaginoidea virens* (Cooke) Takah.<br>Smut, head<br>*Sphacelotheca reiliana* (Kuhn) G. P. Clinton = *Sporisorium holci-sorghi* (Rivolta) K. Vanky<br>Southern corn leaf blight and stalk rot |

TABLE 2-continued

| Plant | Diseases |
|---|---|
| | *Cochliobolus heterostrophus* (Drechs.) Drechs. (anamorph: *Bipolaris maydis* (Nisikado & Miyake) Shoemaker = *Helminthosporium maydis* (Nisikado & Miyake) Southern leaf spot *Stenocarpella macrospora* (Earle) Sutton = *Diplodia macrospora* Earle) Stalk rots, minor *Cercospora sorghi* Ellis & Everh. *Fusarium episphaeria* (Tode) W. C. Snyder & H. N. Hans. *F. merismoides* Corda *F. oxysporum* Schlechtend.:Fr. *F. poae* (Peck) Wollenweb. *F. roseum* Link:Fr. *F. solani* (Mart.) Sacc. (teleomorph: *Nectria haematococca* Berk. & Broome) *F. tricinctum* (Corda) Sacc. *Mariannaea elegans* (Corda) R. A. Samson *Mucor* sp. *Rhopographus zeae* Pat. *Spicaria* sp. Storage rots *Aspergillus* spp. *Penicillium* spp. and other fungi Tar spot* *Phyllachora maydis* Maubl. *Trichoderma* ear rot and root rot *Trichoderma viride* Pers.:Fr. = *T. lignorum* (Tode) (teleomorph: *Hypocrea* sp.) White ear rot, root and stalk rot *Stenocarpella maydis* (Berk.) Sutton = *Diplodia zeae* (Schwein.) Lév. Yellow leaf blight *Ascochyta ischaemi* Sacc. *Phyllosticta maydis* D. C. Arny & R. R. Nelson (teleomorph: *Mycosphaerella zeae-maydis* Mukunya & Boothroyd) Zonate leaf spot *Gloeocercospora sorghi* Bain & Edgerton ex Deighton |
| Cotton (*Gossypium* spp.) | Anthracnose *Glomerella gossypii* Edgerton *Colletotrichum gossypii* Southworth [anamorph] Areolate mildew *Ramularia gossypii* (Speg.) Cif. = *Cercosporella gossypii* Speg. *Mycosphaerella areola* J. Ehrlich & F. A. Wolf [teleomorph] Ascochyta blight *Ascochyta gossypii* Woronichin Black root rot *Thielaviopsis basicola* (Berk. & Broome) Ferraris *Chalara elegans* Nag Raj & Kendrick [synanamorph] Boll rot *Ascochyta gossypii* Woronichin *Colletotrichum gossypii* Southworth *Glomerella gossypii* Edgerton [teleomorph] *Fusarium* spp. *Lasiodiplodia theobromae* (Pat.) Griffon & Maubl. = *Diplodia gossypina* (Cooke) *Botryosphaeria rhodina* (Cooke) Arx [teleomorph] = *Physalospora rhodina* Cooke *Phytophthora* spp. *Rhizoctonia solani* Kühn Charcoal rot *Macrophomina phaseolina* (Tassi) Goidanich Escobilla* *Colletotrichum gossypii* Southworth *Glomerella gossypii* Edgerton [teleomorph] Fusarium wilt *Fusarium oxysporum* Schlechtend.:Fr. *f.* sp. *vasinfectum* (Atk.) W. C. Snyder & H. N. Hans. Leaf spot *Alternaria macrospora* A. Zimmerm. *A. alternata* (FR.:FR.) Keissl. *Cercospora gossypina* Cooke *Mycosphaerella gossypina* (Atk.) Earle [teleomorph] |

TABLE 2-continued

| Plant | Diseases |
|---|---|
| | *Cochliobolus spicifer* R. R. Nelson |
| | *Bipolaris spicifera* (Bainier) Subramanian |
| | [anamorph] = *Curvularia* |
| | *spicifera* (Bainier) Boedijn |
| | *Myrothecium roridum* Tode:Fr |
| | *Rhizoctonia solani* Kühn |
| | *Stemphylium solani* G. F. Weber |
| | Lint contamination |
| | *Aspergillus flavus* Link:Fr. |
| | *Nematospora* spp. |
| | *Nigrospora oryzae* (Berk. & Broome) Petch |
| | *Phymatotrichum* root rot = cotton root rot |
| | *Phymatotrichopsis omnivora* (Duggar) Hennebert = *Phymatotrichum* |
| | *omnivorum* Duggar |
| | Powdery mildew* |
| | *Leveillula taurica* (Lev) G. Arnaud |
| | *Oidiopsis sicula* Scalia [anamorph] = *Oidiopsis* |
| | *gossypii* (Wakef.) Raychaudhuri |
| | *Salmonia malachrae* (Seaver) Blumer & E. Muller |
| | Rust |
| | Cotton rust |
| | *Puccinia schedonnardi* Kellerm. & Swingle |
| | Southwestern cotton rust |
| | *Puccinia cacabata* Arth. & Holw. in Arth. |
| | Tropical cotton rust* |
| | *Phakopsora gossypii* (Lagerh.) Hiratsuka |
| | *Sclerotium* stem and root rot = southern blight |
| | *Sclerotium rolfsii* Sacc. |
| | *Athelia rolfsii* (Curzi) Tu & Kimbrough [teleomorph] |
| | Seedling disease complex |
| | *Colletotrichum gossypii* Southworth |
| | *Fusarium* spp. |
| | *Pythium* spp. |
| | *Rhizoctonia solani* Kühn |
| | *Thanatephorus cucumeris* (A. B. Frank) Donk |
| | [teleomorph] |
| | *Thielaviopsis basicola* (Berk. & Broome) Ferraris |
| | *Chalara elegans* Nag Raj & Kendrick [synanamorph] |
| | Stem canker |
| | *Phoma exigua* Desmaz. |
| | *Verticillium* wilt |
| | *Verticillium dahliae* Kleb. |
| Hop | *Alternaria* cone disorder |
| (*Humulus lupulus* L.) | *Alternaria alternata* (Fr.:Fr.) Keissl. = *Alternaria* |
| | *tenuis* Nees |
| | *Armillaria* root rot (shoestring root rot) |
| | *Armillaria mellea* (Vahl: Fr.) P. Kumm. |
| | (anamorph: *Rhizomorpha subcorticalis* Pers.) |
| | Black root rot |
| | *Phytophthora citricola* Sawada = *P. cactorum* |
| | (Lebert & Cohn) J. Schröt. var. *applanat* |
| | F. Chester |
| | Canker |
| | *Fusarium sambucinum* Fuckel |
| | (teleomorph: *Gibberella pulicaris* (Fr.:Fr.) Sacc.) |
| | Downy mildew |
| | *Pseudoperonospora humuli* (Miyabe & Takah.) G. W. Wils. |
| | Gray mold |
| | *Botrytis cinerea* Pers.:Fr. |
| | (teleomorph: *Botryotinia fuckeliana* (de Bary) Whetzel) |
| | Leaf spots |
| | *Septoria humuli* Westend. = *Ascochyta* |
| | *humuli* Lasch |
| | *Mycocentrospora cantuariensis* (Salmon & Wormald) |
| | Deighton = *Cercospora* |
| | *cantuariensis* Salmon & Wormald |
| | *Phoma* wilt |
| | *Phoma herbarum* Westend. |
| | Powdery mildew |
| | *Sphaerotheca macularis* (Wallr.:Fr.) Lind = *Sphaerotheca* |
| | *humuli* (DC.) Burrill |
| | *Rosellinia* root rot (*Dematophora* root rot) |
| | *Rosellinia necatrix* Prill. |
| | (anamorph: *Dematophora necatrix* R. Hartig) |
| | *Sclerotinia* wilt |
| | *Sclerotinia sclerotiorum* (Lib.) de Bary |
| | *Verticillium* wilt |

TABLE 2-continued

| Plant | Diseases |
|---|---|
| | *Verticillium* albo-atrum Reinke & Berthier |
| | *V. dahliae* Kleb. |
| Oats | Anthracnose |
| (*Avena sativa* L.) | *Colletotrichum graminicola* (Ces.) G. W. Wils. |
| | (teleomorph: *Glomerella graminicola* Politis) |
| | Blast |
| | Unfavorable environmental conditions and/or any of |
| | several pathogens |
| | Downy mildew |
| | *Sclerophthora macrospora* (Sacc.) Thirumalachar et al. |
| | Ergot |
| | *Claviceps purpurea* (Fr.:Fr.) Tul. |
| | (anamorph: *Sphacelia segetum* Lév.) |
| | *Fusarium* foot rot |
| | *Fusarium culmorum* (Wm. G. Sm.) Sacc. |
| | Head blight |
| | *Bipolaris sorokiniana* (Sacc.) Shoemaker |
| | (teleomorph: *Cochliobolus sativus* (Ito & Kuribayashi) |
| | Drechs. ex Dastur) |
| | *Drechslera avenacea* (M. A. Curtis ex Cooke) Shoemaker |
| | *Fusarium graminearum* Schwabe |
| | (teleomorph: *Gibberella zeae* (Schwein.) Petch) |
| | *Fusarium* spp. |
| | Leaf blotch and crown rot (*Helminthosporium* leaf blotch) |
| | *Drechslera avenacea* (M. A. Curtis ex Cooke) Shoemaker = *Helminthosporium* |
| | *avenaceum* M. A. Curtis ex Cooke |
| | *D. avenae* (Eidam) Scharif = *H. avenae* |
| | Eidam |
| | (teleomorph: *Pyrenophora avenae* Ito & Kuribayashi) |
| | Powdery mildew |
| | *Erysiphe graminis* DC. *f.* sp. *avenae* Em. Marchal |
| | *E. graminis* DC. |
| | (anamorph: *Oidium monilioides* (Nees) Link) |
| | *Rhizoctonia* root rot |
| | *Rhizoctonia solani* Kühn |
| | (teleomorph: *Thanatephorus cucumeris* (A. B. Frank) Donk) |
| | Root rot |
| | *Bipolaris sorokiniana* (Sacc.) Shoemaker |
| | *Fusarium* spp. |
| | *Pythium* spp. |
| | *P. debaryanum* Auct. non R. Hesse |
| | *P. irregulare* Buisman |
| | *P. ultimum* Trow |
| | Rust, crown |
| | *Puccinia coronata* Corda |
| | Rust, stem |
| | *Puccinia graminis* Pers. |
| | Seedling blight |
| | *Bipolaris sorokiniana* (Sacc.) Shoemaker |
| | *Drechslera avenae* (Eidam) Scharif |
| | *Fusarium culmorum* (Wm. G. Sm.) Sacc. |
| | *Pythium* spp. |
| | *Rhizoctonia solani* Kühn |
| | Sharp eyespot |
| | *Rhizoctonia cerealis* Van der Hoeven |
| | (teleomorph: *Ceratobasidium cereale* D. Murray & |
| | L. L. Burpee) |
| | Smut, covered |
| | *Ustilago segetum* (Bull.:Pers.) Roussel = *U. kolleri* |
| | Wille |
| | Smut, loose |
| | *Ustilago avenae* (Pers.) Rostr. |
| | Snow mold, pink (*Fusarium* patch) |
| | *Microdochium nivale* (Fr.) Samuel & I. C. Hallett = *Fusarium* |
| | *nivale* Ces. ex Berl. & Voglino |
| | (teleomorph: *Monographella nivalis* (Schaffnit) E. Müller) |
| | Snow mold, speckled or gray (*Typhula* blight) |
| | *Typhula idahoensis* Remsberg |
| | *T. incarnata* Lasch:Fr. |
| | *T. ishikariensis* Imai |
| | Speckled blotch (*Septoria* blight) |
| | *Stagonospora avenae* (A. B. Frank) Bissett = *Septoria* |
| | *avenae* A. B. Frank |
| | (teleomorph: *Phaeosphaeria avenaria* G. F. Weber) |
| | O. Eriksson) |
| | Take-all (white head) |
| | *Gaeumannomyces graminis* (Sacc.) Arx & D. Olivier var. |

TABLE 2-continued

| Plant | Diseases |
|---|---|
| | *avenae* (E. M. Turner) Dennis<br>*G. graminis* (Sacc.) Arx & D. Olivier<br>*Victoria* blight<br>*Bipolaris victoriae* (F. Meehan & Murphy) Shoemaker<br>(teleomorph: *Cochliobolus victoriae* R. R. Nelson) |
| Peanut (*Arachis hypogaea* L.) | *Alternaria* leaf blight<br>*Alternaria tenuissima* (Kunze:Fr.) Wiltshire<br>*Alternaria* leaf spot<br>*Alternaria arachidis* Kulk.<br>*Alternaria* spot and veinal necrosis<br>*Alternaria alternata* (Fr.:Fr.) Keissl.<br>Anthracnose<br>*Colletotrichum arachidis* Sawada (not validly published)<br>*C. dematium* (Pers.) Grove<br>*C. mangenoti* Chevaugeon<br>*Aspergillus* crown rot<br>*Aspergillus niger* Tiegh.<br>Blackhull<br>*Thielaviopsis basicola* (Berk. & Broome) Ferraris<br>(synanamorph: *Chalara elegans* Nag Raj & Kendrick)<br>*Botrytis* blight<br>*Botrytis cinerea* Pers.:Fr.<br>(teleomorph: *Botryotinia fuckeliana* (de Bary) Whetzel)<br>Charcoal rot and *Macrophomina* leaf spot<br>*Macrophomina phaseolina* (Tassi) Goidanich = *Rhizoctonia bataticola* (Tassi) E. J. Butler<br>*Choanephora* leaf spot<br>*Choanephora* spp.<br>Collar rot<br>*Lasiodiplodia theobromae* (Pat.) Griffon & Maubl. = *Diplodia gossypina* Cooke<br>*Colletotrichum* leaf spot<br>*Colletotrichum gloeosporioides* (Penz.) Penz. & Sacc. in Penz.<br>(teleomorph: *Glomerella cingulata* (Stoneman) Spauld. & H. Schrenk)<br>*Cylindrocladium* black rot<br>*Cylindrocladium crotalariae* (C. A. Loos) D. K. Bell & Sobers<br>(teleomorph: *Calonectria crotalariae* (C. A. Loos) D. K. Bell & Sobers)<br>*Cylindrocladium* leaf spot<br>*Cylindrocladium scoparium* Morg.<br>(teleomorph: *Calonectria keyotensis* Terishita)<br>Damping-off, *Aspergillus*<br>*Aspergillus flavus* Link:Fr.<br>*A. niger* Tiegh.<br>Damping-off, *Fusarium*<br>*Fusarium* spp.<br>Damping-off, *Pythium*<br>*Pythium* spp.<br>Damping-off, *Rhizoctonia*<br>*Rhizoctonia* spp.<br>Damping-off, *Rhizopus*<br>*Rhizopus* spp.<br>*Drechslera* leaf spot<br>*Bipolaris spicifera* (Bainier) Subramanian = *Drechslera spicifera* (Bainier) Arx<br>(teleomorph: *Cochliobolus spicifer* R. R. Nelson)<br>*Fusarium* peg and root rot<br>*Fusarium* spp.<br>*Fusarium* wilt<br>*Fusarium oxysporum* Schlechtend.:Fr.<br>Leaf spot, early<br>*Cercospora arachidicola* S. Hori<br>(teleomorph: *Mycosphaerella arachidis* Deighton)<br>Leaf spot, late<br>*Phaeoisariopsis personata* (Berk. & M. A. Curtis) Arx = *Cercosporidium personatum* (Berk. & M. A. Curtis) Deighton<br>(teleomorph: *Mycosphaerella berkeleyi* Jenk.)<br>Melanosis<br>*Stemphylium botryosum* Wallr.<br>(teleomorph: *Pleospora tarda* E. Simmons)<br>*Myrothecium* leaf blight<br>*Myrothecium roridum* Tode:Fr.<br>*Olpidium* root rot |

TABLE 2-continued

| Plant | Diseases |
|---|---|
| | *Olpidium brassicae* (Woronin) P. A. Dang.
Pepper spot and scorch
*Leptosphaerulina crassiasca* (Sechet) C. R. Jackson &
D. K. Bell
*Pestalotiopsis* leaf spot
*Pestalotiopsis arachidis* Satya
*Phoma* leaf blight
*Phoma microspora* Berk. & M. A. Curtis nom. nud. non
Sacc. non Pat. hom. illeg.
*Phomopsis* foliar blight
*Phomopsis phaseoli* (Desmaz.) Sacc. = *P. sojae*
Lehman
(teleomorph: *Diaporthe phaseolorum* (Cooke & Ellis)
Sacc.)
*Phomopsis* leaf spot
*Phomopsis* spp.
*Phyllosticta* leaf spot
*Phyllosticta arachidis-hypogaea* V. G. Rao
*P. sojicola* C. Massal.
(teleomorph: *Pleosphaerulina sojicola* Miura)
*Phymatotrichum* root rot
*Phymatotrichopsis omnivora* (Duggar) Hennebert = *Phymatotrichum
omnivorum* Duggar
Pod rot (pod breakdown)
*Fusarium equiseti* (Corda) Sacc. = *F. scirpi*
Lambotte & Fautrey
(teleomorph: *Gibberella intricans* Wollenweb.)
*F. solani* (Mart.) Sacc.
(teleomorph: *Nectria haematococca* Berk. & Broome)
*Pythium myriotylum* Drechs.
*Rhizoctonia solani* Kühn
(teleomorph: *Thanatephorus cucumeris* (A. Frank) Donk)
Powdery mildew
*Oidium arachidis* Chorin
*Pythium* peg and root rot
*Pythium myriotylum* Drechs.
*P. aphanidermatum* (Edson) Fitzp.
*P. debaryanum* Auct. non R. Hesse
*P. irregulare* Buisman
*P. ultimum* Trow
*Pythium* wilt
*Pythium myriotylum* Drechs.
*Rhizoctonia* foliar blight, peg and root rot
*Rhizoctonia solani* Kühn
Rust
*Puccinia arachidis* Speg.
Scab
*Sphaceloma arachidis* Bitancourt & Jenk.
*Sclerotinia* blight
*Sclerotinia minor* Jagger
*S. sclerotiorum* (Lib.) de Bary
Stem rot (southern blight)
*Sclerotium rolfsii* Sacc.
(teleomorph: *Athelia rolfsii* (Curzi) Tu & Kimbrough)
*Verticillium* wilt
*Verticillium albo-atrum* Reinke & Berthier
*V. dahliae* Kleb.
Web blotch (net blotch)
*Phoma arachidicola* Marasas et al. = *Ascochyta
adzamethica* Schoschiaschvili
(teleomorph: *Didymosphaeria arachidicola* (Chochrjakov)
Alcorn et al. = *Mycosphaerella
arachidicola* Chochrjakov)
Yellow mold
*Aspergillus flavus* Link:Fr.
*A. parasiticus* Speare
Zonate leaf spot
*Cristulariella moricola* (Hino) Redhead
(synanamorph: *Sclerotium cinnomomi* Sawada)
(teleomorph: *Grovesinia pyramidalis* M. Cline et al.) |
| Potato
(*Solanum
tuberosum* L.) | Black dot
*Colletotrichum coccodes* (Wallr.) S. J. Hughes = *C. atramentarium*
(Berk. & Broome) Taubenhaus
Brown spot and Black pit
*Alternaria alternata* (Fries.) Keissler = *A. tenuis*
Ness.
*Cercospora* leaf blotch |

TABLE 2-continued

| Plant | Diseases |
|---|---|
| | *Mycovellosiella concors* (Casp.) Deighton = *Cercospora concors* (Casp.) Sacc.
*Cercospora solani* Thüm
*C. solani-tuberosi* Thirumalachur*
Charcoal rot
*Macrophomina phaseolina* (Tassi) Goidanich = *M. phaseoli* (Maubl.)
*Sclerotium bataticola* Taubenhaus
*Choanephora* blight
*Choanephora cucurbitarum* (Berk. & Rav.) Thaxter
Common rust
*Puccinia pittieriana* P. Henn.
Deforming rust
*Aecidium cantensis* Arthur
Early blight
*Alternaria solani* (E&M) Jones & Grout
*Fusarium* dry rot
*Fusarium* spp.
*F. sambucinum*
*Giberella pulicaris* (Fr.:Fr.) Sacc. [teleomorph] = *Fusarium sulphureum* Schlechtendahl
*F. solani* (Mart.) Sacc. var. *coeruleum* (Lib. ex Sacc.) C. Booth
Other *Fusarium* spp. include: *F. avenaceum* (Fr.) Sacc.
*F. oxysporum* Schlechtend.:Fr.
*F. culmorum* (Wm. G. Sm.) Sacc.
Less common *Fusarium* spp. include: *F. acuminatum* Ellis & Everh.
*F. equiseti* (Corda) Sacc.
*F. crookwellense*
*Fusarium* wilt
*Fusarium* spp.
*F. avenaceum* (Fr.) Sacc.
*F. oxysporum* Schlechtend.:Fr.
*F. solani f.* sp. *eumartii* (Carp.) Snyd and Hans.
Gangrene
*Phoma solanicola f. foveata* (Foister) Malcolmson
*P. foveata* Foister = *P. exigua* var. *foveata* (Foister) Boerema = *P. exigua* Desm. *f.* sp. *foveata* (Foister) Malcolmson & Gray
*P. exigua* Desm. var. *exigua* (more ubiquitous but weaker pathogen)
Gray mold
*Botrytis cinerea* Pers.:Fr.
*Botryotinia fuckeliana* (de Bary) Whetzel [teleomorph]
Late blight
*Phytophthora infestans* (Mont.) de Bary
Leak
*Pythium* spp.
*Pythium ultimum* var. *ultimum* Trow. = *P. debaryanum* R. Hesse
*Pythium aphanidermatum* (Edson) Fitz.
*P. deliense* Meurs
*Phoma* leaf spot*
*Phoma andigena* var. *andina* Turkensteen
Pink rot
*Phytophthora* spp.
*P. cryptogea* Pethybr. & Lafferty
*P. drechsleri* Tucker
*P. erythroseptica* Pethybr.
*P. megasperma* Drechsler
*P. nicotianae* van Breda de Haan var. *parasitica* (Dastur) Waterhouse
*Pleospora herbarum*
*Pleospora herbarum* (Pers. ex Fr.) Rabenh.
*Stemphylium herbarum* E. Simmons [anamorph]
Powdery mildew
*Erysiphe cichoracearum* DC. ex Merat
Powdery scab
*Spongospora subterranea* (Wallr.) Lagerh. *f.* sp. *subterranea* Tomlinson
*Rhizoctonia* canker and black scurf
*Rhizoctonia solani* Kühn
*Thanatephorus cucumeris* (A. B. Frank) Donk |

TABLE 2-continued

| Plant | Diseases |
|---|---|
| | [teleomorph]<br>*Rosellinia* black rot*<br>*Rosellinia* sp.<br>*Dematophora* sp. [anamorph]<br>*Septoria* leaf spot<br>*Septoria lycopersici* Speg. var. *malagutii* Ciccarone &<br>Boerema<br>Silver scurf<br>*Helminthosporium solani* Dur. & Mont.<br>Skin spot<br>*Polyscytalum pustulans* (Owen & Wakef.) Ellis<br>Stem rot (southern blight)<br>*Sclerotium rolfsii* Sacc.<br>*Athelia rolfsii* (Curzi) Tu & Kimbrough [teleomorph]<br>*Thecaphora* smut<br>*Angiosorus solani* (Barrus) Thirum. & O'Brien = *Thecaphora solani* Barrus<br>*Ulocladium* blight<br>*Ulocladium atrum* Preuss<br>*Verticillium* wilt<br>*Verticillium albo-atrum* Reinke & Berthier<br>*V. dahliae* Kleb.<br>Wart<br>*Synchytrium endobioticum* (Schilb.) Perc.<br>White mold<br>*Sclerotinia sclerotiorum* (Lib.) de Bary |
| Rice<br>(*Oryza sativa* L.) | Aggregate sheath spot<br>*Ceratobasidium oryzae-sativae* Gunnell & Webster<br>(anamorph: *Rhizoctonia oryzae-sativae* (Sawada) Mordue)<br>Black kernel<br>*Curvularia lunata* (Wakk.) Boedijn<br>(teleomorph: *Cochliobolus lunatus* R. R. Nelson & Haasis)<br>Blast (leaf, neck [rotten neck], nodal and collar)<br>*Pyricularia grisea* Sacc. = *P. oryzae* Cavara<br>(teleomorph: *Magnaporthe grisea* (Hebert) Barr)<br>Brown spot<br>*Cochliobolus miyabeanus* (Ito & Kuribayashi) Drechs. ex<br>Dastur (anamorph: *Bipolaris oryzae* (Breda de Haan)<br>Shoemaker)<br>Crown sheath rot<br>*Gaeumannomyces graminis* (Sacc.) Arx & D. Olivier<br>Downy mildew<br>*Sclerophthora macrospora* (Sacc.) Thirumalachar et al.<br>Eyespot<br>*Drechslera gigantea* (Heald & F. A. Wolf) Ito<br>False smut<br>*Ustilaginoidea virens* (Cooke) Takah.<br>Kernel smut<br>*Tilletia barclayana* (Bref.) Sacc. & Syd. in Sacc. = *Neovossia horrida* (Takah.) Padwick & A. Khan<br>Leaf smut<br>*Entyloma oryzae* Syd. & P. Syd.<br>Leaf scald<br>*Microdochium oryzae* (Hashioka & Yokogi) Samuels & I. C. Hallett = *Rhynchosporium oryzae* Hashioka & Yokogi<br>Narrow brown leaf spot<br>*Cercospora janseana* (Racib.) O. Const. = *C. oryzae* Miyake<br>(teleomorph: *Sphaerulina oryzina* K. Hara)<br>Pecky rice (kernel spotting)<br>Damage by many fungi including *Cochliobolus miyabeanus* (Ito & Kuribayashi) Drechs. ex Dastur, *Curvularia* spp., *Fusarium* spp., *Microdochium oryzae* (Hashioka & Yokogi) Samuels & I. C. Halett, *Sarocladium oryzae* (Sawada) W. Gams & D. Hawksworth and other fungi.<br>Root rots<br>*Fusarium* spp.<br>*Pythium* spp.<br>*P. dissotocum* Drechs.<br>*P. spinosum* Sawada<br>Seedling blight<br>*Cochliobolus miyabeanus* (Ito & Kuribayashi) Drechs. ex Dastur, *Curvularia* spp., *Fusarium* spp., *Rhizoctonia solani* Kühn, *Sclerotium rolfsii* Sacc.<br>(teleomorph: *Athelia rolfsii* (Curzi) Tu & Kimbrough),<br>and<br>other pathogenic fungi. |

TABLE 2-continued

| Plant | Diseases |
|---|---|
| | Sheath blight<br>*Thanatephorus cucumeris* (A. B. Frank) Donk<br>(anamorph: *Rhizoctonia solani* Kühn)<br>Sheath rot<br>*Sarocladium oryzae* (Sawada) W. Gams & D. Hawksworth = *Acrocylindrium oryzae* Sawada<br>Sheath spot<br>*Rhizoctonia oryzae* Ryker & Gooch<br>Stackburn (*Alternaria* leaf spot)<br>*Alternaria padwickii* (Ganguly) M. B. Ellis<br>Stem rot<br>*Magnaporthe salvinii* (Cattaneo) R. Krause & Webster<br>(synanamorphs: *Sclerotium oryzae* Cattaneo, *Nakataea sigmoidae* (Cavara) K. Hara)<br>Water-mold (seed-rot and seedling disease)<br>*Achlya conspicua* Coker<br>*A. klebsiana* Pieters<br>*Fusarium* spp.<br>*Pythium* spp.<br>*P. dissotocum* Drechs.<br>*P. spinosum* Sawada |
| Rye<br>(*Secale cereale* L.) | Anthracnose<br>*Colletotrichum graminicola* (Ces.) G. W. Wilson<br>(teleomorph: *Glomerella graminicola* Politis)<br>Black head molds<br>*Alternaria* spp.<br>*Cladosporium herbarum* (Pers.:Fr.) Link<br>(teleomorph: *Mycosphaerella tassiana* (De Not.) Johans.)<br>*Epicoccum* spp.<br>*Sporobolomyces* spp.<br>*Stemphylium* spp.<br>Black point<br>*Bipolaris sorokiniana* (Sacc.) Shoemaker<br>(teleomorph: *Cochliobolus sativus* (Ito & Kuribayashi)<br>Drechs. ex Dastur)<br>*Fusarium* spp.<br>Bunt (stinking smut)<br>*Tilletia caries* (DC.) Tul. & C. Tul. = *T. tritici*<br>(Bjerk.) G. Wint. in Rabenh.<br>*T. laevis* Kühn in Rabenh. = *T. foetida*<br>(Wallr.) Liro<br>*Cephalosporium* stripe<br>*Hymenula cerealis* Ellis & Everh. = *Cephalosporium gramineum* Nisikado & Ikata in Nisikado et al.<br>Common root rot and seedling blight<br>*Bipolaris sorokiniana* (Sacc.) Shoemaker = *Helminthosporium sativum* Pammel et al.<br>Cottony snow mold (winter crown rot)<br>*Coprinus psychromorbidus* Redhead & J. A. Traquair<br>Dilophospora leaf spot (twist)<br>*Dilophospora alopecuri* (Fr.:Fr.) Fr.<br>Dwarf bunt<br>*Tilletia controversa* Kühn in Rabenh.<br>Ergot<br>*Claviceps purpurea* (Fr.:Fr.) Tul.<br>(anamorph: *Sphacelia segetum* Lév.)<br>*Fusarium* root rot<br>*Fusarium culmorum* (W. G. Sm.) Sacc.<br>Halo spot<br>*Pseudoseptoria donacis* (Pass.) Sutton = *Selenophoma donacis* (Pass.) Sprague & A. G. Johnson<br>Karnal bunt (partial bunt)<br>*Neovossia indica* (Mitra) Mundkur = *Tilletia indica* Mitra<br>Leaf rust (brown rust)<br>*Puccinia recondita* Roberge ex Desmaz.<br>(anamorph: *Aecidium clematidis* DC.)<br>Leaf streak<br>*Cercosporidium graminis* (Fuckel) Deighton = *Scolicotrichum graminis* Fuckel<br>*Leptosphaeria* leaf spot<br>*Phaeosphaeria herpotrichoides* (De Not.) L. Holm = *Leptosphaeria herpotrichoides* De Not.<br>Loose smut<br>*Ustilago tritici* (Pers.) Rostr.<br>Pink snow mold (*Fusarium* patch) |

TABLE 2-continued

| Plant | Diseases |
|---|---|
| | *Microdochium nivale* (Fr.) Samuels & I. C. Hallet = *Fusarium nivale* Ces. ex Berl. & Voglino (teleomorph: *Monographella nivalis* (Schaffnit) E. Muller) Powdery mildew *Erysiphe graminis* DC. f. sp. Em. Marchal *Pythium* root rot *Pythium aphanidermatum* (Edson) Fitzp. *P. arrhenomanes* Drechs. *P. debaryanum* Auct. non Hesse *P. graminicola* Subramanian *P. ultimum* Trow Scab *Gibberella zeae* (Schwein.) Petch (anamorph: *Fusarium graminearum* Schwabe) Scald *Rhynchosporium secalis* (Oudem.) J. J. Davis Septoria leaf blotch *Septoria secalis* Prill. & Delacr. *Septoria tritici* blotch (speckled leaf blotch) *Septoriatritici* Roberge in Desmaz. (teleomorph: *Mycosphaerella graminicola* (Fuckel) J. Schröt. in Cohn) Sharp eyespot and *Rhizoctonia* root rot *Rhizoctonia cerealis* Van der Hoeven (teleomorph: *Ceratobasidium cereale* D. Murray & L. L. Burpee) Snow scald (*Sclerotinia* snow mold) *Myriosclerotinia borealis* (Bubák. & Vleugel) L. M. Kohn = *Sclerotinia borealis* Bubák. & Vleugel Speckled (or gray) snow mold (*Typhula* blight) *Typhula idahoensis* Remsberg *T. incarnata* Fr. *T. ishikariensis* Imai *T. ishikariensis* Imai var. *canadensis* J. D. Smith & Arsvoll in Arsvoll & J. D. Smith Spot blotch *Bipolaris sorokiniana* (Sacc.) Shoemaker Stagonospora blotch (glume blotch) *Stagonospora nodorum* (Berk.) Castellani & E. G. Germano = *Septoria nodorum* Berk. in Berk. & Broome (teleomorph: *Phaeosphaeria nodorum* (E. Müller) Hedjaroude = *Leptosphaeria nodorum* E. Müller) Stalk smut (stripe smut) *Urocystis occulta* (Wallr.) Rabenh. ex Fuckel Stem rust *Puccinia graminis* Pers.:Pers. = *P. graminis* Pers. f. sp. *secalis* Eriks. & E. Henn. Storage molds *Alternaria* spp. *Aspergillus* spp. *Epicoccum* spp. *Nigrospora* spp. *Penicillium* spp. *Rhizopus* spp. Strawbreaker (eyespot or foot rot) *Pseudocercosporella herpotrichoides* (Fron) Deighton Stripe rust (yellow rust) *Puccinia striiformis* Westend. (anamorph: *Uredo glumarum* J. C. Schmidt) Take-all *Gaeumannomyces graminis* (Sacc.) Arx & Olivier var. *tritici* J. Walker Tan spot (yellow leaf spot) *Pyrenophora tritici-repentis* (Died.) Drechs. (anamorph: *Drechslera tritici-repentis* (Died.) Shoemaker = *Helminthosporium tritici-repentis* Died.) |
| Soybeans (*Glycine max* (L.) Merrill) | *Alternaria* leaf spot *Alternaria* spp. Anthracnose *Colletotrichum truncatum* (Schwein.) Andrus & W. D. Moore *C. dematium* (Pers.) Grove f. *truncatum* (Schwein.) Andrus & W. D. Moore *Glomerella glycines* F. Lehm. & F. A. Wolf |

TABLE 2-continued

| Plant | Diseases |
|---|---|
| | *Colletotrichum destructivum* O'Gara [anamorph]<br>Black leaf blight*<br>*Arkoola nigra* J. Walker & G. Stovold<br>Black root rot<br>*Thielaviopsis basicola* (Berk. & Broome) Ferraris<br>*Chalara elegans* Naj Raj & Kendrick [synanamorph]<br>Brown spot<br>*Septoria glycines* Hemmi<br>*Mycosphaerella usoenskajae* Mashk & Tomil<br>[teleomorph]<br>Brown stem rot<br>*Phialophora gregata* (Allington & D. W. Chamberlain)<br>W. Gams = *Cephalosporium<br>gregatum* Allington & D. W. Chamberlain<br>Charcoal rot<br>*Macrophomina phaseolina* (Tassi) Goidanich<br>*Choanephora* leaf blight<br>*Choanephora infundibulifera* (Currey) Sacc.<br>*C. trispora* (Thaxter)<br>Damping-off<br>*Rhizoctonia solani* Kühn<br>*Thanatephorus cucumeris* (A. B. Frank) Donk<br>[teleomorph]<br>*Pythium aphanidermatum* (Edison) Fitzp.<br>*P. debaryanum* Auct. non R. Hesse<br>*P. irregulare* Buisman<br>*P. myriotylum* Drechs.<br>*P. ultimum* Trow<br>Downy mildew<br>*Peronospora manshurica* (Naumov) Syd. In Gaum.<br>*Drechslera* blight<br>*Drechslera glycines* Narayanasamy & Durairj<br>Frogeye leaf spot<br>*Cercospora sojina* K. Hara<br>*Fusarium* root rot<br>*Fusarium* spp.<br>*Leptosphaerulina* leaf spot<br>*Leptosphaerulina trifolii* (Rostr.) Petr.<br>*Mycoleptodiscus* root rot<br>*Mycoleptodiscus terrestris* (Gerdemann) Ostazeski<br>*Neocosmospora* stem rot<br>*Neocosmospora vasinifecta* E. F. Sm.<br>*Acremonium* sp. [anamorph]<br>*Phomopsis* seed decay<br>*Phomopsis* spp.<br>*Phytophthora* root and stem rot<br>*Phytophthora sojae* Kaufmann & Gerdemann<br>*Phyllosticta* leaf spot<br>*Phyllosticta sojicola* C. Massal<br>*Phymatotrichum* root rot = cotton root rot<br>*Phymatotrichopsis omnivora* (Duggar) Hennebert = *Phymatotrichum<br>omnivorum* Duggar<br>Pod and stem blight<br>*Diaporthe phaseolorum* (Cke. & Ell.) Sacc. var. *sojae*<br>(Lehman) Wehm.<br>*Phomopsis sojae* Lehman [anamorph]<br>Powdery mildew<br>*Microsphaera diffusa* Cooke & Peck<br>Purple seed stain<br>*Cercospora kikuchii* (Mastsumoto & Tomoyasu) M. W. Gardner<br>*Pyrenochaeta* leaf spot*<br>*Pyrenochaeta glycines* Stewart<br>*Pythium* rot<br>*Pythium aphanidermatum* (Edison) Fitzp.<br>*P. debaryanum* Auct. non R. Hesse<br>*P. irregulare* Buisman<br>*P. myriotylum* Drechs.<br>*P. ultimum* Trow<br>Red crown rot<br>*Cylindrocladium crotalariae* (C. A. Loos) D. K. Bell &<br>Sobers<br>*Calonectria crotalariae* (C. A. Loos) D. K. Bell &<br>Sobers<br>[teleomorph]<br>Red leaf blotch = *Dactuliophora* leaf spot*<br>*Dactuliochaeta glycines* (R. B. Stewart) Hartman &<br>Sinclair = *Pyrenochaeta* |

TABLE 2-continued

| Plant | Diseases |
|---|---|
| | *glycines* (R. B. Stewart)<br>*Dactuliophora glycines* Leaky [synanamorph]<br>*Rhizoctonia* aerial blight<br>*Rhizoctonia solani* Kühn<br>*Thanatephorus cucumeris* (A. B. Frank) Donk<br>[teleomorph]<br>*Rhizoctonia* root and stem rot<br>*Rhizoctonia solani* Kühn<br>Rust*<br>*Phakopsora pachyrhizi* Syd.<br>Scab*<br>*Spaceloma glycines* Kurata & Kuribayashi<br>*Sclerotinia* stem rot<br>*Sclerotinia sclerotiorum* (Lib.) deBary<br>Southern blight (damping-off and stem rot) = *Sclerotium* blight<br>*Sclerotium rolfsii* Sacc.<br>*Athelia rolfsii* (Curzi) Tu & Kimbrough [teleomorph]<br>Stem canker<br>*Diaporthe phaseolorum* (Cooke & Ellis) Sacc.<br>*D. phaseolorum* (Cooke & Ellis) Sacc. var. *caulivora*<br>Athow & Caldwell<br>*Phomopsis phaseoli* (Desmaz) Sacc [anamorph]<br>*Stemphylium* leaf blight*<br>*Stemphylium botryosum* Wallr.<br>*Pleospora tarda* (E. Simmons) [teleomorph]<br>Sudden death syndrome<br>*Fusarium solani* (Mart.) Sacc. *f.* sp. *glycines*<br>Target spot<br>*Corynespora cassiicola* (Berk. & M. A. Curtis) C. T. Wei |
| Tobacco<br>(*Nicotiana*<br>tabacum L.) | Anthracnose<br>*Colletotrichum destructivum* O'Gara<br>(teleomorph: *Glomerella glycines* F. Lehm. and F. A. Wolf)<br>Barn spot<br>*Cercospora nicotianae* Ellis & Everh.<br>Barn rot<br>Several fungi and bacteria<br>Black root rot<br>*Thielaviopsis basicola* (Berk. & Broome) Ferraris<br>Black shank<br>*Phytophthora parasitica* Dastur var. *nicotianae* (Breda<br>de<br>Haan) Tucker<br>*P. nicotianae* Breda de Haan var. *nicotianae* G. M. Waterhouse<br>Blue mold (downy mildew)<br>*Peronospora tabacina* D. B. Adam = *P. hyoscyami*<br>de Bary *f.* sp. *tabacina*<br>Brown spot<br>*Alternaria alternata* (Fr.:Fr.) Keissl.<br>Charcoal rot<br>*Macrophomina phaseolina* (Tassi) Goidanich<br>Collar rot<br>*Sclerotinia sclerotiorum* (Lib.) de Bary<br>Damping-off, *Pythium*<br>*Pythium* spp.<br>*P. aphanidermatum* (Edson) Fitzp.<br>*P. ultimum* Trow<br>Frogeye leaf spot<br>*Cercospora nicotianae* Ellis & Everh.<br>*Fusarium* wilt<br>*Fusarium oxysporum* Schlechtend.:Fr. (several *f.* sp.)<br>Gray mold<br>*Botrytis cinerea* Pers.:Fr.<br>(teleomorph: *Botryotinia fuckeliana* (de Bary) Whetzel)<br>*Olpidium* seedling blight<br>*Olpidium brassicae* (Woronin) P. A. Dang.<br>*Phyllosticta* leaf spot<br>*Phyllosticta nicotiana* Ellis & Everh.<br>Powdery mildew<br>*Erysiphe cichoracearum* DC.<br>Ragged leaf spot<br>*Phoma exigua* Desmaz. var. *exigua* = *Ascochyta*<br>*phaseolorum* Sacc.<br>Scab<br>*Hymenula affinis* (Fautrey & Lambotte) Wollenweb. = *Fusarium*<br>*affine* Fautrey & Lambotte<br>Sore shin and damping-off<br>*Rhizoctonia solani* Kühn |

TABLE 2-continued

| Plant | Diseases |
|---|---|
| | (teleomorph: *Thanatephorus cucumeris* (A. B. Frank) Donk) |
| | Southern stem rot (southern blight) |
| | *Sclerotium rolfsii* Sacc. |
| | (teleomorph: *Athelia rolfsii* (Cursi) Tu & Kimbrough) |
| | Stem rot of tranplants |
| | *Pythium* spp. |
| | Target spot |
| | *Rhizoctonia solani* Kühn |
| | *Verticillium* wilt |
| | *Verticllium albo-atrum* Reinke & Berthier |
| | *V. dahliae* Kleb. |
| Wheat | Alternaria leaf blight |
| (*Triticum* spp. L.) | *Alternaria triticina* Prasada & Prabhu |
| | Anthracnose |
| | *Colletotrichum graminicola* (Ces.) G. W. Wils. |
| | *Glomerella graminicola* Politis [teleomorph] |
| | Ascochyta leaf spot |
| | *Ascochyta tritici* S. Hori & Enjoji |
| | Aureobasidium decay |
| | *Microdochium bolleyi* (R. Sprague) DeHoog & |
| | Hermanides-Nijhof = *Aureobasidium* |
| | *bolleyi* (R. Sprague) Arx |
| | Black head molds = sooty molds |
| | *Alternaria* spp. |
| | *Cladosporium* spp. |
| | *Epicoccum* spp. |
| | *Sporobolomyces* spp. |
| | *Stemphylium* spp. |
| | and other genera |
| | Black point = kernel smudge |
| | associated with various fungi and physiological |
| | circumstances |
| | Cephalosporium stripe |
| | *Hymenula cerealis* Ellis & Everh. = *Cephalosporium* |
| | *gramineum* Nisikado & Ikata in Nisikado |
| | et al |
| | Common bunt = stinking smut |
| | *T. tritici* (Bjerk.) G. Wint. in Rabenh. = *Tilletia* |
| | *caries* (DC.) Tul. & C. Tul. |
| | *T. laevis* Kühn in Rabenh. = *T. foetida* |
| | (Wallr.) Liro |
| | Common root rot |
| | *Bipolaris sorokiniana* (Sacc.) Shoemaker |
| | *Cochliobolus sativus* (Ito & Kuribayashi) Drechs. Ex |
| | Dast. |
| | [teleomorph] |
| | Cottony snow mold |
| | *Coprinus psychromorbidus* Redhead & Traquair |
| | Crown rot = foot rot, seedling blight, dryland root rot |
| | *Fusarium* spp. |
| | *F. pseudograminearum* O'Donnell et. T. Aoki sp. nov. |
| | *Gibberella zeae* (Schwein.) Petch |
| | *F. graminearum* Schwabe, Group II [anamorph] |
| | *G. avenacea* R. J. Cook |
| | *F. avenaceum* (Fr.:Fr.) Sacc. [anamorph] |
| | *F. culmorum* (W. G. Smith) Sacc. |
| | Dilophospora leaf spot = twist |
| | *Dilophospora alopecuri* (Fr.)Fr. |
| | Downy mildew = crazy top |
| | *Sclerophthora macrospora* (Sacc.)Thirumalachar et al. |
| | Dwarf bunt |
| | *Tilletia controversa* Kühn in Rabenh |
| | Ergot |
| | *Claviceps purpurea* (Fr.:Fr.) Tul. |
| | *Sphacelia segetum* Lév. [anamorph] |
| | Eyespot = foot rot, strawbreaker |
| | *Tapesia yallundae* Wallwork & Spooner |
| | *Ramulispora herpotrichoides* (From) Arx [anamorph] = *Pseudocercosporella* |
| | *herpotrichoides* (Fron) Deighton |
| | *T. acuformis* (Boerema, Pieters & Hamers) Crous |
| | *Ramulispora acuformis* (Nirenberg) Crous [anamorph] = *Pseudocercosporella* |
| | *herpotrichoides* var. *acuformis* |
| | Nirenberg |
| | False eyespot |
| | *Gibellina cerealis* Pass. |
| | Flag smut |
| | *Urocystis agropyri* (G. Preuss) Schrot. |

TABLE 2-continued

| Plant | Diseases |
|---|---|
| | Foot rot = dryland foot rot
*Fusarium* spp.
Halo spot
*Pseudoseptoria donacis* (Pass.) Sutton = *Selenophoma donacis* (Pass.) R. Sprague & A. G. Johnson
Karnal bunt = partial bunt
*Tilletia indica* Mitra = *Neovossia indica* (M. Mitra) Mundk.
Leaf rust = brown rust
*Puccinia triticina* Eriks. = *P. recondita* Roberge ex Desmaz. f. sp. *tritici*
(Eriks. &
E. Henn.) D. M. Henderson
*P. tritici-duri* Viennot-Bourgin
*Leptosphaeria* leaf spot
*Phaeosphaeria herpotrichoides* (De Not.) L. Holm = *Leptosphaeria herpotrichoides* De Not.
*Stagonospora* sp. [anamorph]
Loose smut
*Ustilago tritici* (Pers.) Rostr. = *U. segetum tritici*, *U. segetum nuda*, *U. segetum avena*
*Microscopica* leaf spot
*Phaeosphaeria microscopica* (P. Karst.) O. Eriksson = *Leptosphaeria microscopica* P. Karst
*Phoma* spot
*Phoma* spp.
*P. glomerata* (Corda) Wollenweb. & Hochapfel
*P. sorghina* (Sacc.) Boerema et al. = *P. insidiosa* Tassi
Pink snow mold = *Fusarium* patch
*Microdochium nivale* (Fr.) Samuels & I. C. Hallett = *Fusarium nivale* Ces. ex Berl. & Voglino
*Monographella nivalis* (Schaffnit) E. Müller [teleomorph]
*Platyspora* leaf spot
*Clathrospora pentamera* (P. Karst.) Berl. = *Platyspora pentamera* (P. Karst.) Wehmeyer
Powdery mildew
*Erysiphe graminis* DC. f. sp. tritici Em. Marchal
*Blumeria graminis* (DC.) E. O. Speer = *E. graminis* DC.
*Oidium monilioides* (Nees) Link [anamorph]
*Pythium* root rot
*Pythium aphanidermatum* (Edison) Fitzp.
*P. arrhenomanes* Drechs.
*P. graminicola* Subramanian
*P. myriotylum* Drechs
*P. volutum* Vanterpool & Truscot
*Rhizoctonia* root rot
*Rhizoctonia solani* Kühn
*Thanatephorus cucumeris* (A. B. Frank) Donk [teleomorph]
Ring spot = Wirrega blotch
*Pyrenophora semeniperda* (Brittlebank & Adam) Schoemaker = *Drechslera campanulata* (Lev.) Sutton
*D. wirreganesis* Wallbork, Lichon & Sivanesan
Scab = head blight
*Fusarium* spp.
*Gibberella zeae* (Schwein.) Petch
*Fusarium graminearum* Schwabe, Group II [anamorph]
*G. avenacea* R. J. Cook
*F. avenaceum* (Fr.:Fr.) Sacc. [anamorph]
*F. culmorum* (Wm. G. Sm.) Sacc.
*Microdochium nivale* (Fr.) Samuels & I. C. Hallett = *F. nivale* Ces ex Berl. & Voglino
*Monographella nivale* (Schaffnit) E. Müller [teleomorph]
*Sclerotinia* snow mold = snow scald
*Myriosclerotinia borealis* (Bubák & Vleugel) L. M. Kohn = *Sclerotinia borealis* Bubák & Vleugel
*Sclerotium* wilt (see Southern blight)
*Sclerotium rolfsii* Sacc.
*Athelia rolfsii* (Curzi) Tu & Kimbrough [teleomorph]
*Septoria* blotch
*Septoria tritici* Roberge in Desmaz.
*Mycosphaerella graminicola* (Fuckel) J. Schröt. In |

TABLE 2-continued

| Plant | Diseases |
|---|---|
| | Cohn [teleomorph] |
| | Sharp eyespot |
| | *Rhizoctonia cerealis* Van der Hoeven |
| | *Ceratobasidium cereale* D. Murray & L. L. Burpee |
| | [teleomorph] |
| | Snow rot |
| | *Pythium* spp. |
| | *P. aristosporum* Vanterpool |
| | *P. iwayamai* Ito |
| | *P. okanoganense* Lipps |
| | Southern blight = *Sclerotium* base rot |
| | *Sclerotium rolfsii* Sacc. |
| | *Athelia rolfsii* (Curzi) Tu & Kimbrough [teleomorph] |
| | Speckled snow mold = gray snow mold or *Typhula* blight |
| | *Typhula idahoensis* Remsberg |
| | *T. incarnata* Fr. |
| | *T. ishikariensis* Imai |
| | *T. ishikariensis* Imai var. *canadensis* Smith & Arsvoll |
| | Spot blotch |
| | *Bipolaris sorokiniana* (Sacc.)Shoemaker |
| | *Stagonospora* blotch |
| | *Phaeosphaeria avenaria* (G. F. Weber) O. Eriksson *f.* sp. |
| | *triticea* T. Johnson |
| | *Stagonospora avenae* (A. B. Frank) Bissett *f.* sp. |
| | *tritica* |
| | T. Johnson [anamorph] = *Septoria* |
| | *avenae* A. B. Frank *f.* sp. *triticea* T. Johnson |
| | *Phaeosphaeria nodorum* (E. Müller) Hedjaroude |
| | *Stagonospora nodorum* (Berk.) Castellani & E. G. Germano |
| | [anamorph] = *Septoria* |
| | *nodorum* (Berk.) Berk. in Berk. & Broome |
| | Stem rust = black rust |
| | *Puccinia graminis* Pers.:Pers. = *P. graminis* |
| | Pers.:Pers. *f.* sp. *tritici* Eriks. & E. Henn. |
| | Storage molds |
| | *Aspergillus* spp. |
| | *Penicillium* spp. |
| | and others |
| | Stripe rust = yellow rust |
| | *Puccinia striiformis* Westend. |
| | *Uredo glumarum* J. C. Schmidt [anamorph] |
| | Take-all |
| | *Gaeumannomyces graminis* (Sacc.) Arx & D. Olivier var. |
| | *tritici* J. Walker |
| | *G. graminis* (Sacc.) Arx & D. Olivier var. *avenae* (E. M. Turner) |
| | Dennis |
| | Tan spot = yellow leaf spot, red smudge |
| | *Pyrenophora tritici-repentis* (Died.) Drechs. |
| | *Drechslera tritici-repentis* (Died.) Shoemaker |
| | [anamorph] |
| | Tar spot |
| | *Phyllachora graminis* (Pers.:Fr.) Nitschke |
| | *Linochora graminis* (Grove) D. G. Parbery [anamorph] |
| | Zoosporic root rot |
| | *Lagena radicicola* Vant & Ledingham |
| | *Ligniera pilorum* Fron & Gaillat |
| | *Olpidium brassicae* (Woronin) Dang. |
| | *Rhizophydium graminis* Ledingham |
| Cultivated Wild Rice (*Zizania palustris* L.) | Anthracnose |
| | *Colletotrichum sublineolum* |
| | Ergot |
| | *Claviceps zizaniae* |
| | Fungal brown spot |
| | *Bipolaris oryzae* |
| | *Phytophthora* crown and root rot |
| | *Phytophthora erythroseptica* |
| | Scab |
| | *Fusarium* spp. |
| | Spot blotch |
| | *Bipolaris sorokiniana* |
| | Stem rot |
| | *Sclerotium hydrophilum* |
| | *Sclerotium oryzae* |

TABLE 2-continued

| Plant | Diseases |
|---|---|
| | Stem smut |
| | *Entyloma lineatum* |
| | Zonate eye spot |
| | *Drechslera gigantea* |

Various publications and sequences are cited herein, which are hereby incorporated by reference in their entireties.

The invention claimed is:

1. A method of producing a plant cell resistant to a phytopathogenic fungus, comprising the following steps:
   a) introducing into a plant cell a construct comprising:
      a promoter regulatory sequence that is functional in the plant cell, operably linked to
      a DNA sequence which, when it is transcribed, generates an RNA molecule comprising at least a sense sequence and an antisense sequence which are at least partially complementary, said sense sequence comprising a sequence essentially homologous to a fungal gene essential to the fungus or to its phytopathogenicity, said antisense sequence comprising a sequence essentially homologous to the sequence complementary to said fungal gene, wherein said RNA molecule targets said fungal gene, and
      a terminator regulatory sequence, resulting in a transformed plant cell;
   b) placing the transformed cell in culture under conditions that allow the transcription of the construct, and
   c) selecting the transformed cell that is resistant to the phytopathogenic fungus.

2. A method of producing a plant resistant to a phytopathogenic fungus, comprising the step of regenerating a plant from the transformed cell of claim 1.

3. The method of claim 1, wherein the selection step in performed before the transformed cell is placed in culture under conditions that allow the transcription of the construct.

4. The method of claim 1 wherein the sense and antisense nucleotide sequences are separated by a polynucleotide that does not exhibit any homology with the fungal gene.

5. The method of claim 1 wherein the sense and antisense nucleotide sequences have different sizes.

6. The method of claim 1 wherein the fungal gene is a gene essential to the fungus.

7. The method of claim 6, wherein the fungal gene is chosen from the group consisting of erg11, erg6, aur1, ipt, ef2, ef3, met4, met30, ilv5, and a gene encoding beta-tubulin.

8. The method of claim 7, wherein the fungal gene is gene encoding beta-tubulin.

9. The method of claim 8, wherein the DNA sequence is represented by the sequence identifier SEQ ID No. 4.

10. The method of claim 9, wherein the plant is tobacco and the phytopathogenic fungus is *Cercospora nicotianae*.

11. The method of claim 1, wherein the fungal gene is a gene essential to the pathogenicity of the fungus.

12. The method of claim 11, wherein the fungal gene is chosen from the group consisting of tri5, fum5, 763, a gene encoding polygalacturonase, and a buf gene.

13. The method of claim 12, wherein the fungal gene is a buf gene.

14. The method of claim 13, wherein the DNA sequence is represented by the sequence identifier SEQ ID No. 13.

15. The method of claim 14, wherein the plant is rice and the phytopathogenic fungus is *Magnaporthe grisea*.

16. A plant cell resistant to a phytopathogenic fungus, comprising
a construct comprising
a promoter regulatory sequence that is functional in the plant, operably linked to
a DNA sequence which, when it is transcribed, generates an RNA molecule comprising at least a sense sequence and an antisense sequence which are at least partially complementary, said sense sequence comprising a sequence essentially homologous to a fungal gene essential to the fungus or to its phytopathogenicity, said antisense sequence comprising a sequence essentially homologous to the sequence complementary to said essential fungal gene, wherein said RNA molecule targets said fungal gene, and
a terminator regulatory sequence.

17. The plant cell of claim 16, which is contained in a plant which is resistant to a phytopathogenic fungus.

18. The plant cell of claim 16, wherein the sense and antisense nucleotide sequences are separated by a polynucleotide that does not exhibit any homology with the target gene.

19. The plant cell of claim 16, wherein the sense and antisense nucleotide sequences have different sizes.

20. The plant cell of claim 16, wherein the fungal gene is a gene essential to the fungus.

21. The plant cell of claim 16, wherein the fungal gene is chosen from the group consisting of erg11, erg6, aur1, ipt, ef3, ef2, met4, met30, ilv5, and a gene encoding beta-tubulin.

22. The plant cell of claim 16, wherein the fungal gene is a gene encoding beta-tubulin.

23. The plant cell of claim 16, wherein the DNA sequence is represented by the sequence identifier SEQ ID No. 4.

24. The plant cell of claim 16, wherein the fungal gene is a gene essential to the pathogenicity of the fungus.

25. The plant cell of claim 16, wherein the fungal gene is chosen from the group consisting of tri5, fum5, 763, a gene encoding polygalacturonase, and a buf gene.

26. The plant cell of claim 25, wherein the fungal gene is a buf gene.

27. The plant cell of claim 26, wherein the DNA sequence is represented by the sequence identifier SEQ ID No. 13.

28. The plant of claim 17, which is a monocotyledon.

29. The plant of claim 28, which is selected from the group consisting of wheat, maize and rice.

30. The plant of claim 29, which is a rice plant resistant to *Magnaporthe grisea*, wherein the DNA sequence is represented by the sequence identifier SEQ ID No. 13.

31. The plant of claim 17, which is a dicotyledon.

32. The plant of claim 31, which is selected from the group consisting of rapeseed, soybean, tobacco and cotton.

33. The plant of claim 32 which is a tobacco plant resistant to *Cercospora nicotianae*, wherein the DNA sequence is represented by the sequence identifier SEQ ID No. 4.

34. A method for identifying a gene essential to the development or to the pathogenicity of a phytopathogenic fungus, comprising the following steps:
a) transforming a plant cell or a plant with a construct comprising:
a promoter regulatory sequence that is functional in the plant cell or plant, operably linked to
a DNA sequence which, when it is transcribed, generates an RNA molecule comprising at least a sense sequence and an antisense sequence which are at least partially complementary, said sense sequence comprising a sequence essentially homologous to a phytopathogenic fungus gene, said antisense sequence comprising a sequence essentially homologous to the sequence complementary to said phytopathogenic fungus gene, wherein said RNA molecule targets said phytopathogenic fungus gene and
a terminator regulatory sequence,
b) bringing the cells or the plants thus transformed into contact with the phytopathogenic fungus,
c) studying the resulting phenotype, and
d) characterizing the gene corresponding to the sequence of nucleotides thus inserted.

35. A method for inhibiting the expression of a fungal gene, comprising the following steps:
a) transforming a plant cell with a construct comprising:
a promoter regulatory sequence that is functional in the plant cell, operably linked to
a DNA sequence which, when it is transcribed, generates an RNA molecule comprising at least a sense sequence and an antisense sequence which are at least partially complementary, said sense sequence comprising a sequence essentially homologous to a fungal gene essential to the fungus or to its phytopathogenicity, said antisense sequence comprising a sequence essentially homologous to the sequence complementary to said fungal gene, wherein said RNA molecule targets said fungal gene,
a terminator regulatory sequence,
b) placing the cell thus transformed in culture under conditions that allow the transcription of said construct, and
c) allowing the plant cell to contact the fungus.

36. The method of claim 35, comprising an additional step of regenerating the transformed cell to form a plant.

* * * * *

UNITED STATES PATENT AND TRADEMARK OFFICE
CERTIFICATE OF CORRECTION

| | | |
|---|---|---|
| PATENT NO. | : 7,741,531 B2 | Page 1 of 1 |
| APPLICATION NO. | : 11/471956 | |
| DATED | : June 22, 2010 | |
| INVENTOR(S) | : Rachel Baltz et al. | |

It is certified that error appears in the above-identified patent and that said Letters Patent is hereby corrected as shown below:

In Claim 8, line 1 (column 78, line 56) insert the word --a-- before the second occurrence of the word "gene".

Signed and Sealed this

Seventh Day of September, 2010

David J. Kappos
*Director of the United States Patent and Trademark Office*